US008636955B2

(12) United States Patent
Chakravarty et al.

(10) Patent No.: US 8,636,955 B2
(45) Date of Patent: Jan. 28, 2014

(54) PACKAGED CHIP FOR MULTIPLEXING PHOTONIC CRYSTAL WAVEGUIDE AND PHOTONIC CRYSTAL SLOT WAVEGUIDE DEVICES FOR CHIP-INTEGRATED LABEL-FREE DETECTION AND ABSORPTION SPECTROSCOPY WITH HIGH THROUGHPUT, SENSITIVITY, AND SPECIFICITY

(75) Inventors: Swapnajit Chakravarty, Austin, TX (US); Ray T. Chen, Austin, TX (US); Amir Hosseini, Austin, TX (US)

(73) Assignee: Omega Optics, Inc., Austin, TX (US)

( * ) Notice: Subject to any disclaimer, the term of this patent is extended or adjusted under 35 U.S.C. 154(b) by 0 days.

(21) Appl. No.: 13/607,801

(22) Filed: Sep. 9, 2012

(65) Prior Publication Data

US 2013/0005606 A1  Jan. 3, 2013

Related U.S. Application Data

(63) Continuation-in-part of application No. 12/462,311, filed on Aug. 3, 2009, now Pat. No. 8,293,177, and a continuation-in-part of application No. 12/806,840, filed on Aug. 23, 2010, now Pat. No. 8,282,882.

(51) Int. Cl.
*G01N 21/00* (2006.01)
(52) U.S. Cl.
USPC .................. 422/82.11; 422/82.09; 385/12
(58) Field of Classification Search
USPC ............ 422/400, 127, 82.09, 82.11; 385/123, 385/124, 129, 132, 43; 356/477, 478, 480, 356/481
See application file for complete search history.

(56) References Cited

U.S. PATENT DOCUMENTS

| | | | |
|---|---|---|---|
| 4,148,556 A | 4/1979 | Sauter et al. | |
| 5,689,597 A | 11/1997 | Besse | |
| 5,852,691 A | 12/1998 | Mackie | |
| 6,400,490 B1 | 6/2002 | Hosoi | |
| 6,571,038 B1 | 5/2003 | Joyner et al. | |
| 7,113,677 B2 | 9/2006 | Doi et al. | |
| 7,734,122 B1 | 6/2010 | Mackie | |
| 8,189,968 B2 | 5/2012 | Chen et al. | |
| 2002/0048422 A1* | 4/2002 | Cotteverte et al. | 385/4 |
| 2006/0280405 A1* | 12/2006 | Gunn et al. | 385/37 |

OTHER PUBLICATIONS

Zou Y et al., "Methods to array photonic crystal microcavities for high throughput high sensitivity biosensing on a silicon-chip based platform", Lab Chip 12, 2309 (2012).
Lai W-C. et al., "Silicon nano-membrane based photonic crystal microcavities for high sensitivity bio-sensing", Optics Lett. 37(7), 1208 (2012).
Chakravarty S. et al., "Slow light engineering for high Q high sensitivity photonic crystal microcavity biosensors in silicon", Biosens. Bioelectron. 38(1), 170 (2012).
Chakravarty S. et al,"On-chip sensing of volatile organic compounds in water by hybrid polymer and silicon photonic-crystal slot-waveguide devices",Proc.SPIE 8258,825815(2012).

(Continued)

*Primary Examiner* — Natalia Levkovich
(74) *Attorney, Agent, or Firm* — Taboada Law Firm, PLLC; John M. Taboada

(57) ABSTRACT

Systems and methods for chip-integrated label-free detection and absorption spectroscopy with high throughput, sensitivity, and specificity are disclosed. The invention comprises packaged chips for multiplexing photonic crystal waveguide and photonic crystal slot waveguide devices. Other embodiments are described and claimed.

31 Claims, 40 Drawing Sheets

(56) References Cited

OTHER PUBLICATIONS

Lai W-C. et al, "On-chip methane sensing by near-IR absorption signatures in a photonic crystal slot waveguide", Optics Lett. 36(6), 984 (2011).

Lai W-C. et al, "Photonic crystal slot waveguide absorption spectrometer for on-chip near-infrared spectroscopy of xylene in water", Appl. Phys. Lett. 98, 0223304 (2011).

* cited by examiner

Along F-F'

Along G-G'

Combined Output with separated absolute wavelength spans covered by 205, 206, 207 and 208

PACKAGED CHIP FOR MULTIPLEXING PHOTONIC CRYSTAL WAVEGUIDE AND PHOTONIC CRYSTAL SLOT WAVEGUIDE DEVICES FOR CHIP-INTEGRATED LABEL-FREE DETECTION AND ABSORPTION SPECTROSCOPY WITH HIGH THROUGHPUT, SENSITIVITY, AND SPECIFICITY

I. CROSS REFERENCE TO RELATED APPLICATIONS

The application is a continuation-in-part application of U.S. patent application Ser. No. 12/462,311, titled "Photonic Crystal Microarray Device for Label-Free Multiple Analyte Sensing, Biosensing and Diagnostic Assay Chips", filed Aug. 3, 2009 and U.S. patent application Ser. No. 12/806,840, title "Photonic Crystal Slot Waveguide Miniature On-Chip Absorption Spectrometer", filed Aug. 23, 2010, the contents of which are hereby incorporated by reference.

II. BACKGROUND

1. Field of the Invention

This invention relates generally to the field of packaged chip integrated optical devices, for chip-integrated infrared optical absorption spectroscopy as well as chip-integrated label-free biomolecule microarray. The apparatus and method enables high throughput sensing as well as high specificity.

2. Background of the Invention

Label-free biosensors are particularly attractive since they avoid complex chemistries caused by steric hindrance of the labels. All methods of detection in lab-on-chip platforms at present transduce the specific binding of the biomolecule of interest to its specific conjugate biomolecule receptor bound to the device substrate, into an electrical, mechanical, or optical signal. Optical detection techniques are generally preferred due to their freedom from electromagnetic interference. While several platforms based on ring resonators, wire waveguides, and surface plasmon resonance (SPR) have been investigated, photonic crystal (PC) microcavities, in general, are more compact (of the order of a few square microns in surface area) and have higher sensitivity than other devices due to slow light effect and the larger optical mode overlap with the analyte within compact optical mode volume. Much of the research in the literature concerns single PC microcavity biosensors. Methods to array two-dimensional PC microcavities have primarily focused on the detection of a single bio-molecular probe binding to its specific conjugate target biomolecule on all microcavities. A method to array photonic crystal microcavities along a single photonic crystal waveguide was previously presented in U.S. patent application Ser. No. 12/462,311. Here, we disclose novel methods to array these PC microcavities using multimode interference optical power splitters which can be combined to create large chip-integrated microarrays in which all PC microcavity sensors, each coated with a different biomolecule target receptor, can be simultaneously interrogated with the same small quantity of probe sample, resulting in high throughout diagnostic assays. The multiplexed detection not only achieves high throughput detection, but the ability to measure many biomolecule interactions at the same instant of time allows one to do the actual test experiments and the control experiments and further multiplex these experiments to achieve higher statistical confidence regarding the specificity of the binding reactions. Sandwich assays can also be performed on the same platform to confirm binding specificity.

In addition, chip integrated optical absorption spectrometers are attractive since they allow chemical and biological analytes to be distinguished on a chip with near-infrared optical absorption signatures. Photonic crystal slot waveguide have been demonstrated as viable agents to perform chip-integrated optical absorption spectroscopy. However, in a photonic crystal slot waveguide, the wavelength range over which light is slowed down as it propagates down the photonic crystal waveguide is small. To increase the wavelength bandwidth over which slow light phenomenon is achieved and thus enable a wide bandwidth, infrared optical absorption spectrometer on chip, it is necessary to multiplex several photonic crystal slot waveguides. A method that couples light into all the photonic crystal slot waveguides simultaneously and thus measures the analyte absorption spectrum across a broad wavelength range on-chip is desired.

III. SUMMARY

One embodiment of the invention provides a sensor comprising a semiconductor material slab with high dielectric constant, supported on the bottom by a cladding with dielectric constant lower than the slab. The bottom cladding is supported by the semiconductor substrate. The core in the slab is defined by the path via which light propagates in the slab. A multimode interference power splitter (MMI) is defined which splits the power from a single input ridge or rib waveguide into multiple (n) output ridge or rib waveguides where n=1, 2 . . . N. The MMI structure is a rectangular mesa defined in the slab, each MMI having a single input ridge or rib waveguide and several n=1, 2 . . . N output ridge or rib waveguides. The ridge waveguide on each output arm of the MMI in the first stage can further input light into a cascaded MMI in the second stage and succeeding stages. The number of cascaded stages is m where m=1, 2 . . . M. On each output arm of the $m^{th}$ cascaded MMI, a photonic crystal pattern is defined as a triangular lattice of holes, with a lattice constant $\alpha$, etched into the slab. The photonic crystal waveguide is defined by filling a single row of air holes, from input ridge waveguide transition to output ridge waveguide transition with the semiconductor slab material. This is equivalent to stating that a row of air holes from the input ridge waveguide to the output ridge waveguide is missing. Alternatively, when holes are etched in a triangular lattice into the slab, a row of the triangular lattice from the input ridge waveguide transition to output ridge waveguide transition is not etched. A photonic crystal microcavity is similarly defined by filing a few holes with semiconductor slab material. This is equivalent to stating that a few holes are missing. Alternatively, when holes are etched in a triangular lattice into the slab, a few holes of the triangular lattice are not etched in order to form a photonic crystal microcavity. On each output arm of the MMI that has a photonic crystal waveguide, one or more (p) where p=1, 2 . . . P, photonic crystal microcavities are patterned at a distance of y lattice periods from the photonic crystal waveguide, where y=1, 2, 3, 4, 5, 6, or 7. The center-to-center distance between individual photonic crystal microcavities is 50 microns. Light is coupled into the first stage MMI via a ridge waveguide. Light is out-coupled from the output ridge waveguides of the last cascaded stage MMI into photonic crystal waveguides which finally end in M×N output ridge waveguides. The total number of photonic crystal microcavity sensors simultaneously interrogated is thus M×N×P. When a broadband light source is input into the MMI, it splits the light into its output arms in the same ratio among all arms as 1/N. The intensity of light in each output arm is thus determined by the number of output arms. After M cascaded stages, the normalized intensity of light input into a photonic crystal waveguide is 1/(M×N). On each output arm which has a photonic crystal waveguide, wavelengths corresponding to the resonant wavelengths of the individual microcavities are coupled to the corresponding microcavities. As a result, minima are observed in the transmission spectrum corresponding to the dropped wavelength of each photonic crystal microcavity. Depending upon the wavelength range of interrogation, the period of the lattice, $\alpha$, can vary from 50 nm to 1500 nm and the etch depth of the lattice structure, which is equal to the height of the semiconductor slab, can vary from 0.4 to 0.7 times the lattice periodicity above. The semiconductor slab material can be silicon (or any Group IV material), gallium arsenide (or any III-V semiconductor) or any semiconductor material with high refractive index. The substrate can be any Group IV material corresponding to the Group IV core material, or any substrate suitable to grow the III-V slab material. The bottom cladding can be silicon dioxide, silicon nitride or any material with dielectric constant lower than the dielectric constant of the slab. Thus, multiple photonic crystal microcavities are not only arrayed along the length of the same photonic crystal waveguide on each arm, but on each output arm of the MMI. Since light is slowed down as it propagates down the photonic crystal waveguide, there arises a group index mismatch between the light that propagates down the photonic crystal waveguide and the light fed into the photonic crystal waveguide from the input ridge waveguide. A similar group index mismatch exists at the interface between the output end of the photonic crystal waveguide and the output ridge waveguide. Due to the index mismatch, Fresnel reflections occur from the ridge waveguide-photonic crystal waveguide facet. It is therefore necessary to design a group index taper that minimizes reflection and thus couples the light efficiently from the input ridge waveguide into the photonic crystal waveguide as well as couples light out efficiently from the photonic crystal waveguide to the output ridge waveguide. The group index taper, or impedance tapers, at both the input and the output of the photonic crystal waveguide are formed by shifting away the first s row of air holes where s=1, 2, 3 ... 32 away from the photonic crystal waveguide, normal to the photonic crystal waveguide in the plane of the slab varying in linear steps from sqrt($3\alpha$) to 1.08 times sqrt($3\alpha$) over s steps where s=1, 2, 3 ... 32, where $\alpha$ is the lattice constant of the photonic crystal lattice. On each of the M×N output arms of the last cascaded stage of the MMI, the lattice constant of the triangular lattice photonic crystal may be the same or different. When the lattice constant of the triangular lattice photonic crystal are different, the absolute resonance frequency of the photonic crystal microcavity in each arm are different. Hence the absolute wavelength of the resonance frequency that is measured at each output sub-wavelength grating coupler is different. Consequently, the ridge waveguides that precede each output sub-wavelength grating coupler can be combined either by cascaded Y-junctions or through cascaded multimode interference power combiners, and terminated in a single output sub-wavelength grating coupler, without any overlap between the absolute resonance wavelengths from each photonic crystal microcavity. As a result, all resonances of all the photonic crystal microcavities can be measured from a single output sub-wavelength grating coupler. The sub-wavelength grating couplers at both the input and the output have a periodicity $\beta$ in one direction in the plane of the slab and a periodicity $\gamma$ in the direction orthogonal to $\beta$ in the plane of the slab.

Above the microcavity, a thin film of target biomolecules are immobilized on the microcavity surface. Each microcavity surface is coated with an exclusive target receptor molecule or biomolecule to form the dielectric coating. Since the target biomolecules are dispensed by ink-jet printing, the thin film of target biomolecules also coats on the inner surfaces of the columnar members in the immediate vicinity of the photonic crystal microcavity. The one or more binding molecules are free of detection labels. The one or more target biomolecules may also be tagged with fluorescent, radioactive, or magnetic labels. In order to immobilize the target biomolecules, when the slab material is silicon, a thin layer of silicon dioxide is left on the silicon slab at the time of fabrication. The silicon dioxide surface is then functionalized by treating with 10% by volume 3-aminopropyl-triethoxy-silane (3-APTES) in toluene. It is then washed 3 times in toluene to ensure complete removal of unbound 3-APTES, 3 times in methanol to remove toluene, and finally 3 times in de-ionized water to remove methanol. The device is then incubated in 1% glutaraldehyde in phosphate buffered saline (PBS) for 5 minutes and washed 3 times in PBS and ink jet printed with target antibodies (Abs) in glycerol. The printed spots were left to incubate overnight. Subsequently, all target Abs not bound to the functionalized device layer were removed by washing 3 times in PBS. The washing steps are completed in a few seconds, which ensures that unbound target Abs do not have sufficient time to bind to undesired areas which would result in cross-talk.

The one or more specific binding substances are thus arranged in an array on the microcavities, along the photonic crystal waveguide. A single transmission spectrum from each output arm of the MMI therefore probes the binding events on multiple P microcavities on a single photonic crystal waveguide. The transmission spectrum from all the output arms of all M stages of the 1×N MMI thus gives the result of binding events from M×N×P photonic crystal microcavities at any given instant of time. In this way, high throughput measurement is achieved without the need for re-alignment of optics after each measurement. A binding event on a specific microcavity changes the resonance frequency of the photonic crystal microcavity. Since the resonance frequency of the photonic crystal microcavity is dropped from the transmission of the photonic crystal waveguide, a change in the resonance of the photonic crystal microcavity changes the dropped frequency/wavelength from the photonic crystal waveguide transmission and thus shifts the corresponding transmission minimum and leads to a sensing event for the specific microcavity. The change in resonance frequency of each photonic crystal microcavity is exclusive to the binding events between the target biomolecule coating the specific photonic crystal microcavity and its conjugate probe biomolecule in the sample analyte that is introduced, and is independent of the resonance frequency characteristics of other photonic crystal microcavities on the same photonic crystal waveguide or on other photonic crystal waveguides in other parallel cascaded arms of the MMI. Analyzed probe biomolecules can be proteins, DNA, RNA, small molecules, or genes. The light is input into the chip through only one ridge waveguide at the input of the first MMI in the first stage of the cascade. Thus simultaneous mutually exclusive measurements from M×N×P photonic crystal microcavities are obtained simultaneously leading to high throughput sensing measurements.

Signal amplification as well as specific detection is achieved at low concentrations by incorporating a sandwich immunoassay technique. The target receptor molecule that is bound to the microcavity surface is designated as a primary target receptor. A resonance wavelength shift occurs when a probe biomolecule attaches to the primary target receptor. A secondary target biomolecule which also binds specifically to the probe biomolecule, when introduced, now causes an additional secondary resonance wavelength shift. In this way, the secondary target verifies that the biomolecule that has bound to the primary target receptor is in fact the probe biomolecule. By monitoring the resonance wavelength shifts, the specificity of binding is confirmed. No resonance wavelength shift shall be observed upon introduction of either the probe biomolecule or the secondary target antibodies, on a second photonic crystal microcavity in the array which is coated with a control biomolecule such as bovine serum albumin (BSA). No resonance wavelength shift shall be observed upon introduction of either the probe biomolecule or the secondary target antibodies, on a third photonic crystal microcavity in the array which is coated with an isotype matched control biomolecule. The specificity of the assay is thus verified from the results on three photonic crystal microcavities. In addition to the secondary resonance wavelength shift caused by the binding of the secondary target to the probe biomolecule, the lack of any resonance wavelength shift in the control photonic crystal microcavities confirms the specificity. In one preferred embodiment, more than one photonic crystal microcavity is coated with the same primary target receptor. At the same time, more than one photonic crystal microcavity is coated separately with the same or different control biomolecule or isotype matched control to the primary target receptor. Specificity is thus justified by the simultaneous binding and none thereof in the multiplexed sandwich arrangement. The secondary target that binds to the primary probe biomolecule adds to the primary resonance wavelength shift of the probe biomolecule to the primary target receptor, thereby leading to signal amplification for enhanced device sensitivity.

Another embodiment of the invention provides a sensor comprising a semiconductor material slab with high dielectric constant, supported on the bottom by a cladding with dielectric constant lower than the slab. The bottom cladding is supported by the semiconductor substrate. The core in the slab is defined by the path via which light propagates in the slab. An MMI is defined which splits the power from a single input ridge or rib waveguide into multiple (n) output ridge or rib waveguides where n=1, 2 . . . N. The ridge waveguide on each output arm of the MMI in the first stage can further input light into a cascaded MMI in the second stage and succeeding stages. The number of cascaded stages is m where m=1, 2 . . . M. On each output arm of the $m^{th}$ cascaded MMI, a photonic crystal pattern is defined as a triangular lattice of holes, with a lattice constant $\alpha$, etched into the slab. The photonic crystal waveguide is defined by filling a single row of air holes, from input ridge waveguide transition to the output ridge waveguide transition with the semiconductor slab material. One or more rectangular slots or voids are etched within each photonic crystal waveguide. The photonic crystal waveguide together with the one or more slots that extend along the length of the photonic crystal waveguide define the photonic crystal slot waveguide. The slot extends into the ridge waveguides at both the input and output end of the photonic crystal slot waveguide. A slot mode converter transitions the optical mode from the regular ridge waveguide to the slotted ridge waveguide at both the input and the output end. The slow light guiding wavelength range of each photonic crystal slot waveguide is small. In order to increase the wavelength bandwidth of the device over which slow light guiding is achieved, each photonic crystal waveguide on each M×N ridge waveguide has a different lattice constant for the triangular lattice. In this way, the guided mode transmission bandwidth of each photonic crystal waveguide is different and thus slow light guiding is achieved over a wider wavelength range. Light is coupled into the first stage MMI via a ridge waveguide. Light is out-coupled from the output ridge waveguides of the last cascaded stage MMI into slotted ridge waveguides via mode converters and then into photonic crystal slot waveguides. Each photonic crystal slot waveguide terminates into a slotted ridge waveguide which finally end in M×N output ridge waveguides after a slot mode converter section.

The MMI sections (including all cascaded stages) and all ridge waveguides are covered with a cover polymer which is optically transparent in the wavelength range over which transmission measurements are performed and has a lower dielectric constant than the slab in the wavelength range over which transmission measurements are performed. For instance, in one embodiment where the slab is made of silicon and the bottom cladding is made of silicon dioxide and the substrate is silicon, and optical transmission measurements are performed in the wavelength range of 1.2 to 1.7 microns, the cover polymer can be SU-8 (Microchem). One skilled in the art will note that the cover polymer can be any optically transparent low loss polymer in the wavelength range between 1.2 to 1.7 microns. An opening is made in the cover polymer by photolithography so that the photonic crystal waveguide regions are totally exposed. In this way, analytes interact with the device in the photonic crystal patterned regions only. In one instance, the analytes interact with the biomolecules coated on top of the photonic crystal microcavities leading to changes in resonance transmission characteristics of the photonic crystal waveguides. In another instance, the analytes fill the void slot or slots within the photonic crystal waveguides and cause a change in the transmitted intensity down the photonic crystal slot waveguides dependent on the absorbance of the analyte that fills the void slot.

The input arm of the MMI in the first stage has a sub-wavelength grating coupler made from a rectangular array of rectangular slots or voids etched into the slab. Each of the M×N output ridge waveguides at the output of the photonic crystal waveguides in each of the M×N output arms has a sub-wavelength grating coupler made from a rectangular array of rectangular slots or voids etched into the slab. The sub-wavelength grating couplers enable light to be coupled via external single mode optical fibers into and out of the ridge waveguides. The sub-wavelength grating couplers at both the input and output may be coated with optically transparent polymer in the wavelength range of transmission, for instance SU-8 (Microchem). One skilled in the art will note that the cover polymer can be any optically transparent low loss polymer in the wavelength range between 1.2 to 1.7 microns.

A microscope glass slide, typically 500 microns thick with a rectangular opening is then bonded to the cover polymer SU-8 (Microchem). One skilled in the art will note that the top glass slide can also be another bare silicon wafer or a silicon wafer with a silicon dioxide or silicon nitride coating or any other semiconductor wafer such as gallium arsenide, indium phosphide, or sapphire that can be bonded to the cover polymer, and is thus referred henceforth as a rigid dielectric layer. Analytes enter into the chip through the rectangular void and the rigid dielectric layer provides a rugged support for the chip, comprising the substrate, bottom cladding and slab with patterned device elements in the slab. Yet, in some embodiments, the rigid dielectric layer may be absent and analytes interact with the photonic crystal waveguides and photonic crystal slot waveguides directly through the opening in the cover polymer.

In one embodiment, light is incident on the sub-wavelength grating couplers from the top via external optical fibers. In one instance light from the optical fiber is incident through the rigid dielectric and the optically transparent cover polymer layers. In another instance, light from the optical fiber is incident from the top on the sub-wavelength grating couplers from external optical fibers through a hole etched in the rigid dielectric, but through the optically transparent cover polymer. In another instance, light from the optical fiber is incident from the top via external optical fibers through a hole etched in the rigid dielectric as well as an opening made in the cover polymer via photolithography in the same step that a hole is opened into the cover polymer to expose the photonic crystal waveguide regions. Light from the sub-wavelength grating couplers on the output ridge waveguides is coupled out from the output photonic crystal waveguides in the same way as the input coupling of the input optical fiber to the input sub-wavelength grating couplers. The embodiment describes using optical fibers, however, one skilled in the art will note that light can be input via the sub-wavelength grating couplers from external lasers and output via the sub-wavelength grating couplers to external optical detectors. One skilled in the art will also note that the external optical fiber can be attached to the input and output sub-wavelength grating couplers via ultra-violet cured polymer such as epoxy.

In another embodiment, light from an external optical fiber is incident onto the sub-wavelength grating couplers from the bottom of the substrate through a slot or void that is completely etched through the substrate to the bottom cladding. Light from the sub-wavelength grating couplers on the output ridge waveguides is coupled out from the output photonic crystal waveguides in the same way from the bottom through the substrate as the input coupling of the input optical fiber to the input sub-wavelength grating couplers. The embodiment describes the method using optical fibers, however, one skilled in the art will note that light can be input via the sub-wavelength grating couplers from external lasers and output via the sub-wavelength grating couplers to external optical detectors.

The semiconductor chip comprising the substrate, the bottom cladding, the slab with the device elements, the cover polymer, and the rigid dielectric layer are placed in a package made of ceramic or plastic. The package has holes that allow the optical fibers or the external light source to interface with the sub-wavelength grating couplers. The rectangular ceramic package is patterned at the four corners with grooves that enable precision positioning of the semiconductor chip with the external measurement setup containing the external input and output optical fibers. The input and output optical fibers in the external measurement setup are precisely aligned to deliver and collect light respectively at maximum efficiency from the input and output sub-wavelength grating couplers.

To Summarize:

The primary objective of the invention is to provide a packaged integrated chip for multiplexing photonic crystal microcavity coupled waveguide sensors and photonic crystal slot waveguide absorption sensors with compact size that can be monolithically integrated to implement a personalized diagnostic microarray chip and a chip-integrated optical absorption spectrometer respectively. The objective is to build a custom package to efficiently couple light into and out of the chip-integrated sensors from external sources.

The second objective of the invention is to significantly increase measurement throughput from devices by signal collection and analysis from multiple elements of a microarray in photonic crystal microcavity coupled waveguide sensors and photonic crystal slot waveguide absorption sensors in a single measurement as opposed to individual element measurement in contemporary systems.

Other objectives and advantages of the present invention will become apparent from the following descriptions, taken in connection with the accompanying drawings, wherein, by way of illustration and example, an embodiment of the present invention is disclosed.

IV. BRIEF DESCRIPTION OF THE DRAWINGS

The drawings constitute a part of this specification and include exemplary embodiments of the present invention, which may be embodied in various forms. It is to be understood that in some instances various aspects of the present invention may be shown exaggerated or enlarged to facilitate an understanding of the invention.

A more complete and thorough understanding of the present invention and benefits thereof may be acquired by referring to the following description together with the accompanying drawings, in which like reference numbers indicate like features, and wherein:

FIG. 1 is a schematic top view drawing showing the design of a microarray device based on a 1×N MMI, with a single input and N outputs. Each output arm can cascade into the input arm of a second stage MMI or in subsequent cascades to an $M^{th}$ stage MMI. The number of output ridge waveguides after the last stage MMI is thus M×N. On each output arm M×N, a photonic crystal waveguide is present and an array of P photonic crystal microcavities are coupled to that photonic crystal waveguide. In FIG. 1, N is chosen as 4 and M is chosen as 2 and P is chosen arbitrarily as 1 or 2. P can be equal to P=1, 2, 3, 4, 5, or 6 photonic crystal microcavities along the length of a single photonic crystal waveguide on each arm of the MMI. Sub-wavelength grating couplers at the input and output, couple light from external optical sources into the optical waveguides.

Figure 12:
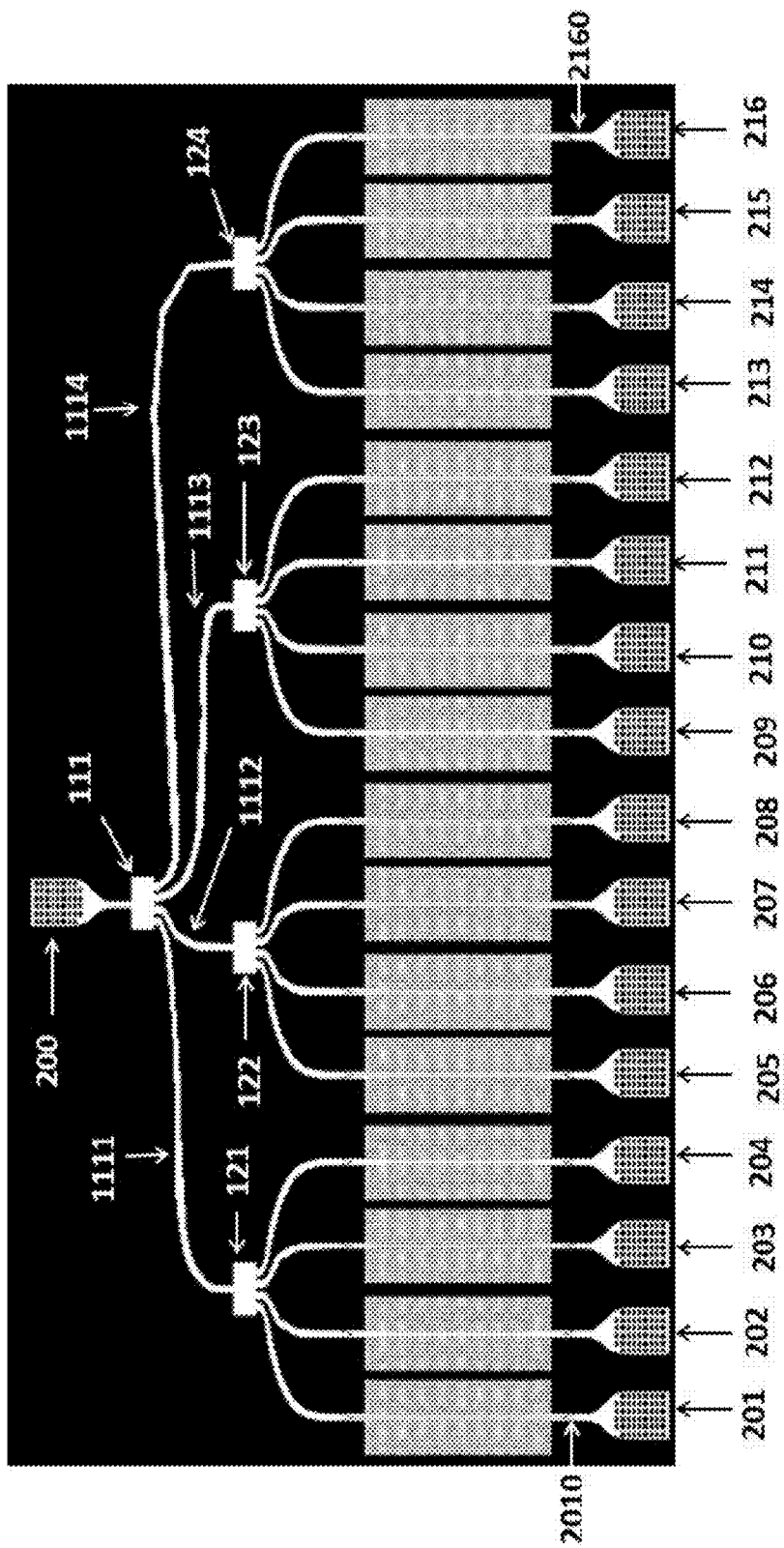

FIG. 12 is a schematic top view showing the design of a photonic crystal slot waveguide array device based on a 1×N MMI, with a single input and N outputs. Each output arm can cascade into the input arm of a second stage MMI or in subsequent cascades to an $M^{th}$ stage MMI. The number of output ridge waveguides after the last stage MMI is thus M×N. Photonic crystal slot waveguides are defined on each $(M \times N)^{th}$ waveguide.

Figure 13:
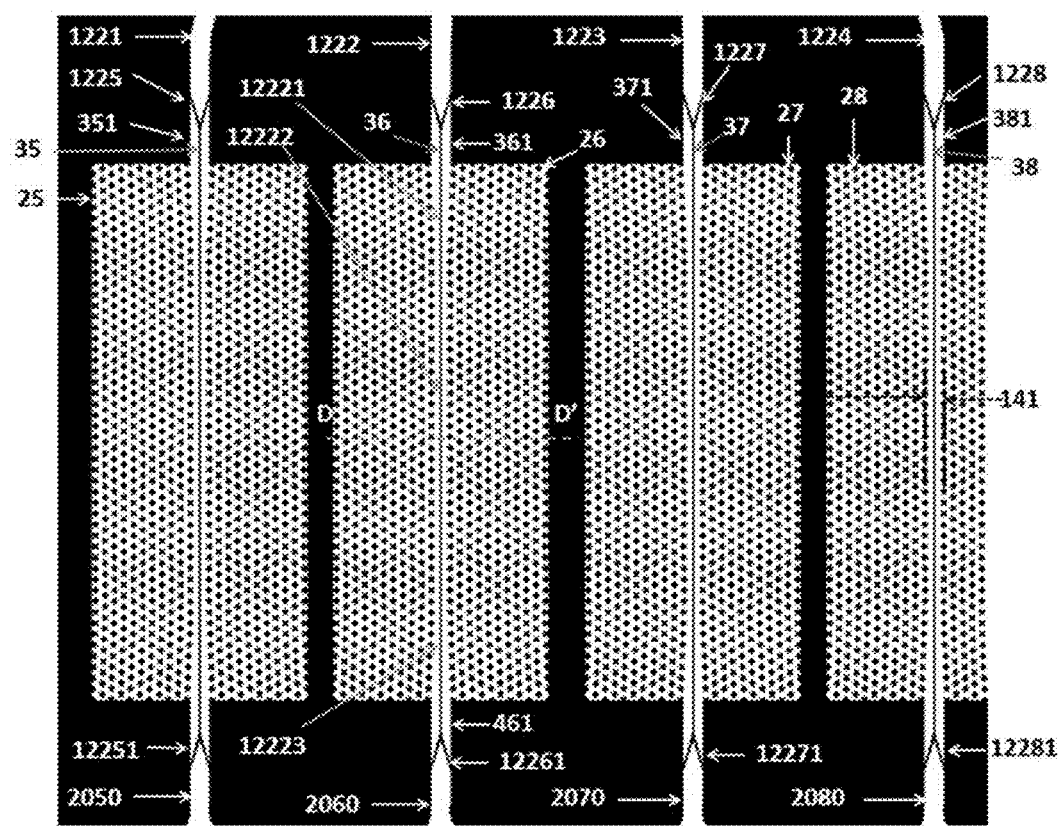

FIG. 13 is an enlarged top view showing the photonic crystal slot waveguide device that is arrayed in the package.

Figure 14:
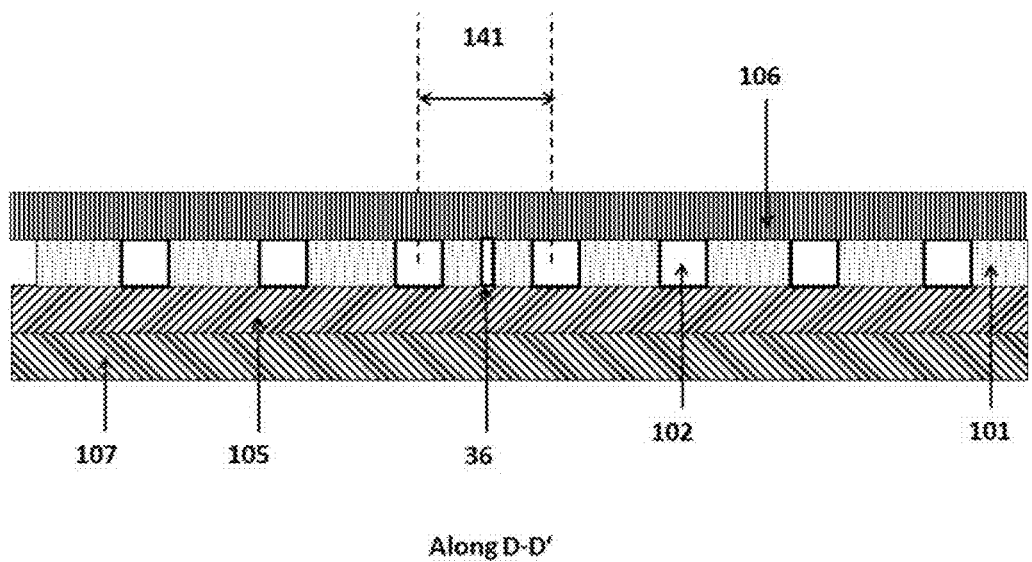

FIG. 14 is a cross-section of the device in FIG. 13 along the plane D-D'.

Figure 15:
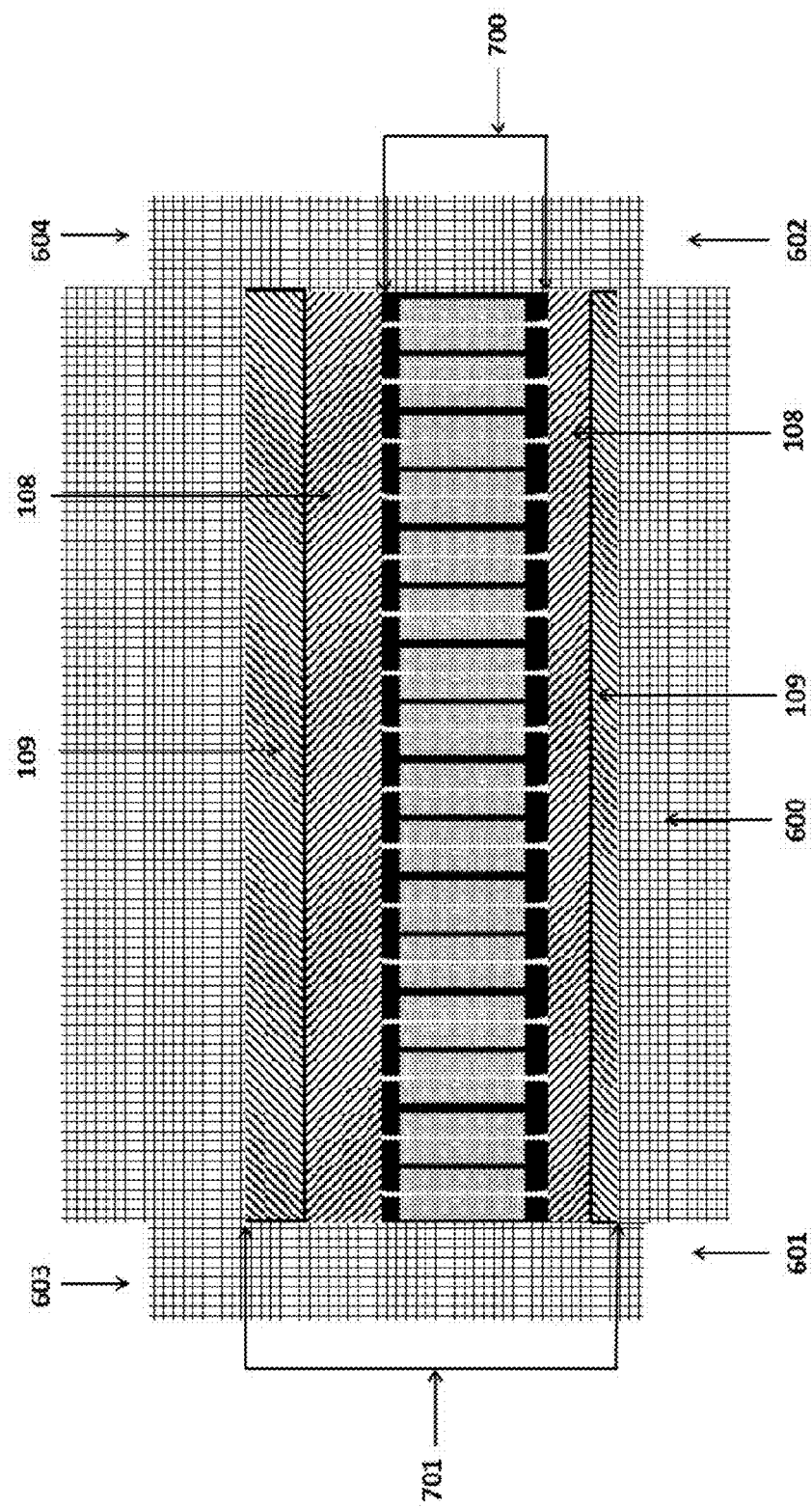

FIG. 15 is top view of the arrayed device within an outer package.

Figure 16:
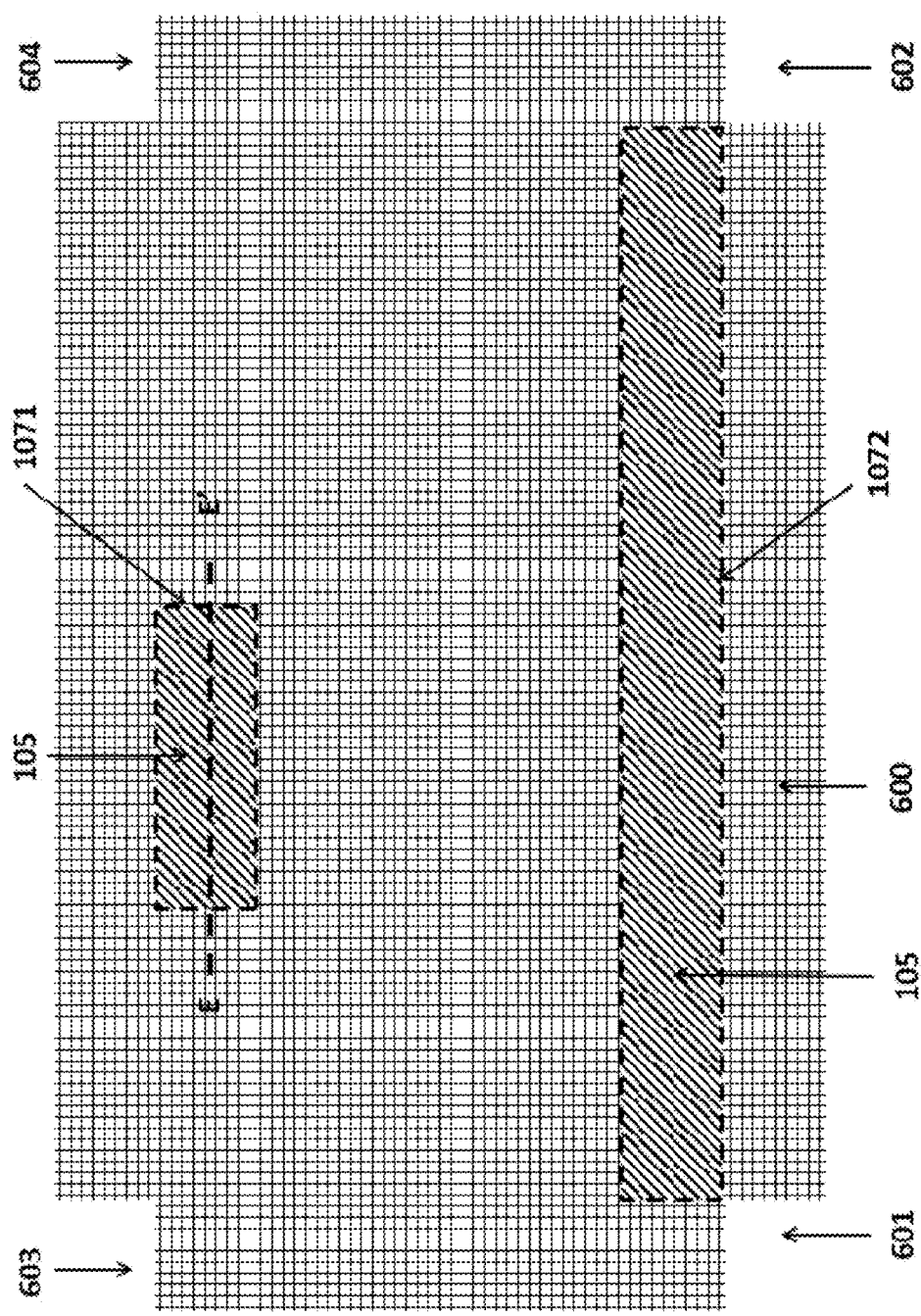

FIG. 16 is bottom view of the outer package showing the opening through which light is coupled from external optical sources into the chip.

Figure 17:
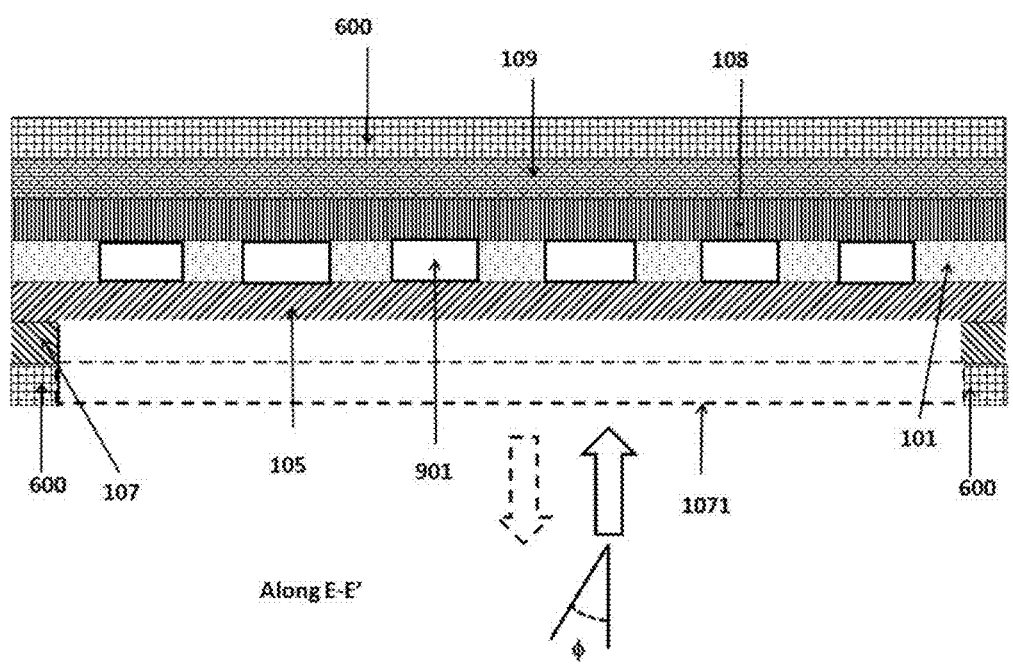

FIG. 17 is cross-section view of the package with the chip inside along the plane E-E' in FIG. 16.

Figure 18:
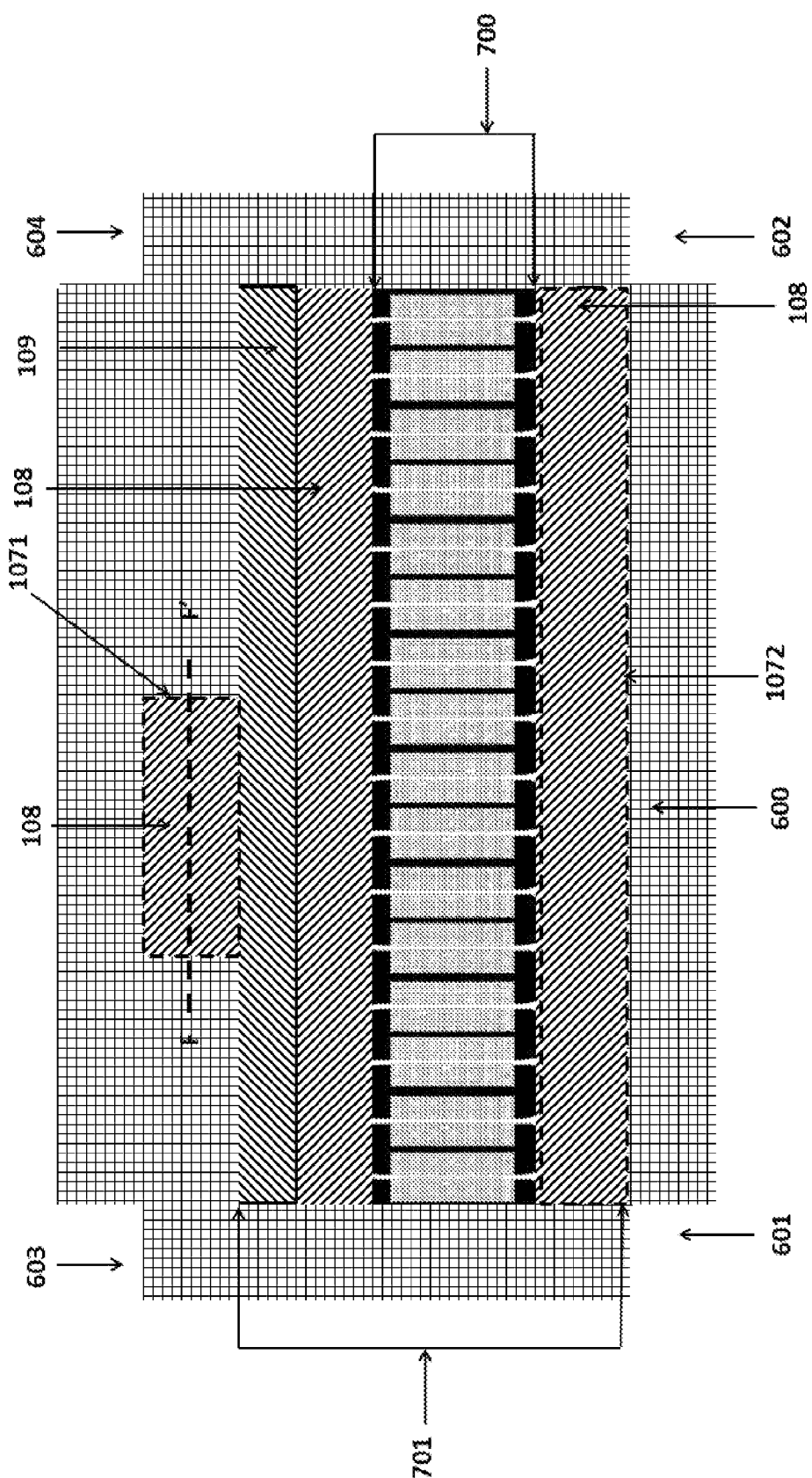

FIG. 18 is a top view of the arrayed device within an outer package in a second embodiment in which the light is incident and also exits the chip from the top. Light is incident on the input sub-wavelength grating coupler through a cover polymer overlayer. Light exits from the output sub-wavelength grating couplers through the cover polymer overlayer to the detector.

Figure 19:
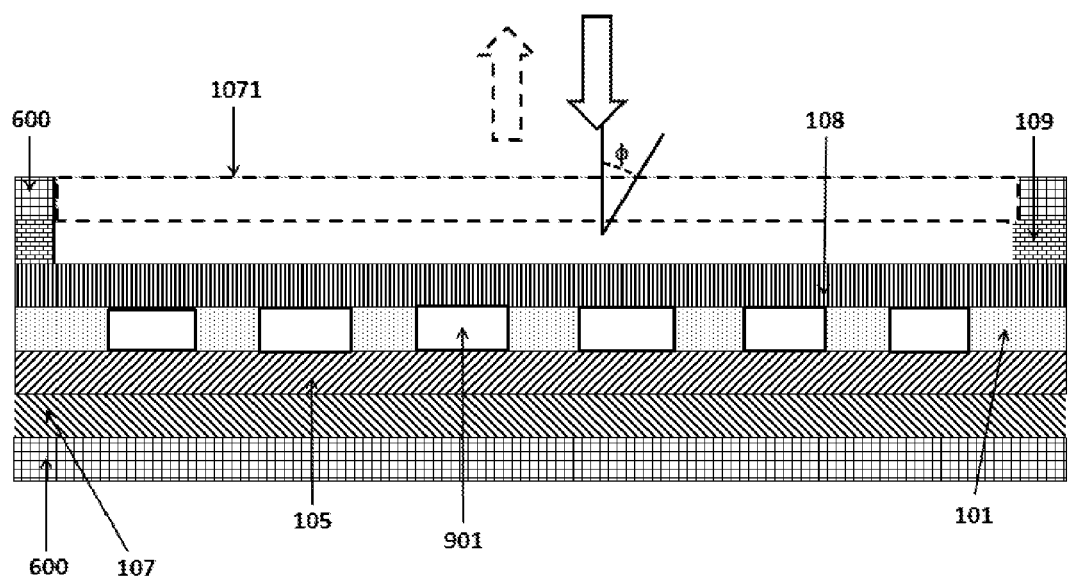

FIG. 19 is a cross-section view of the package with the chip inside along the plane F-F' in FIG. 18 for the case of the second embodiment where the light is incident from the top and is also collected from the top of the chip.

Figure 20:
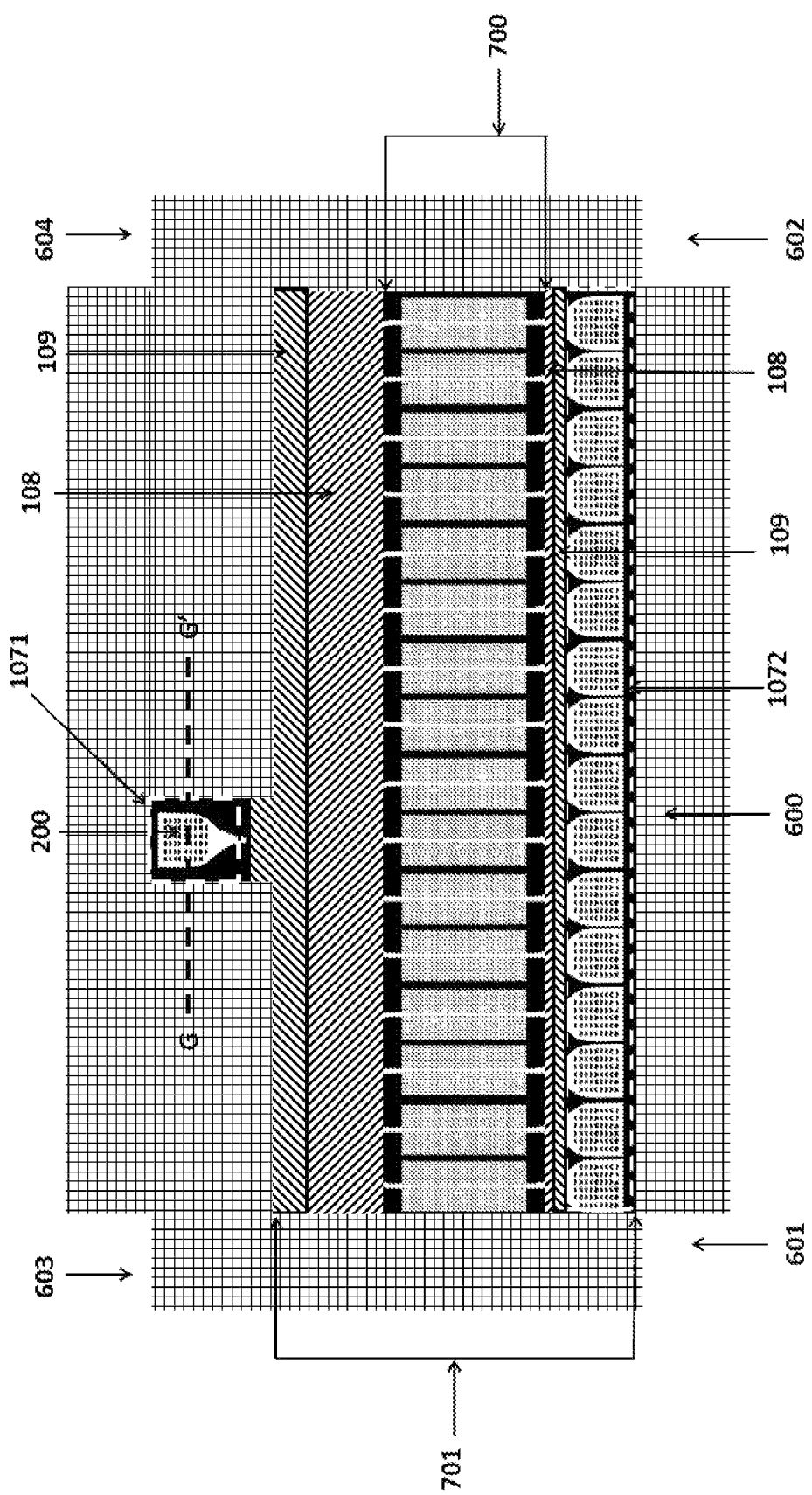

FIG. 20 is a top view of the arrayed device within an outer package in a third embodiment in which the light is incident and also exits the chip from the top. Light is incident directly on the input sub-wavelength grating coupler. Light exits directly from the output sub-wavelength grating couplers to the detector.

Figure 21:
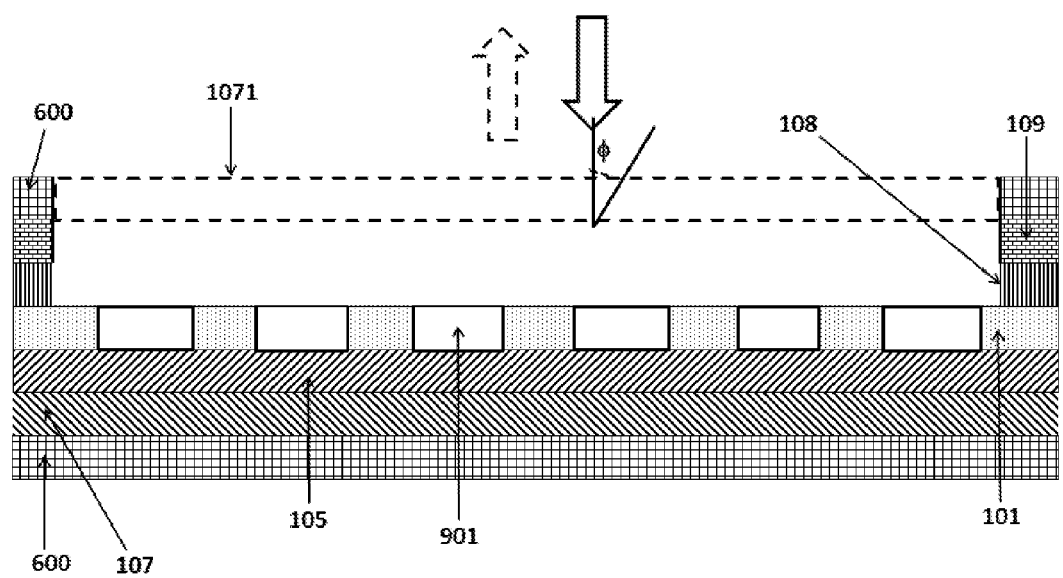

FIG. 21 is a cross-section view of the package with the chip inside along the plane G-G' in FIG. 20 for the case of the third embodiment where the light is incident from the top and is also collected from the top of the chip.

Figure 22:
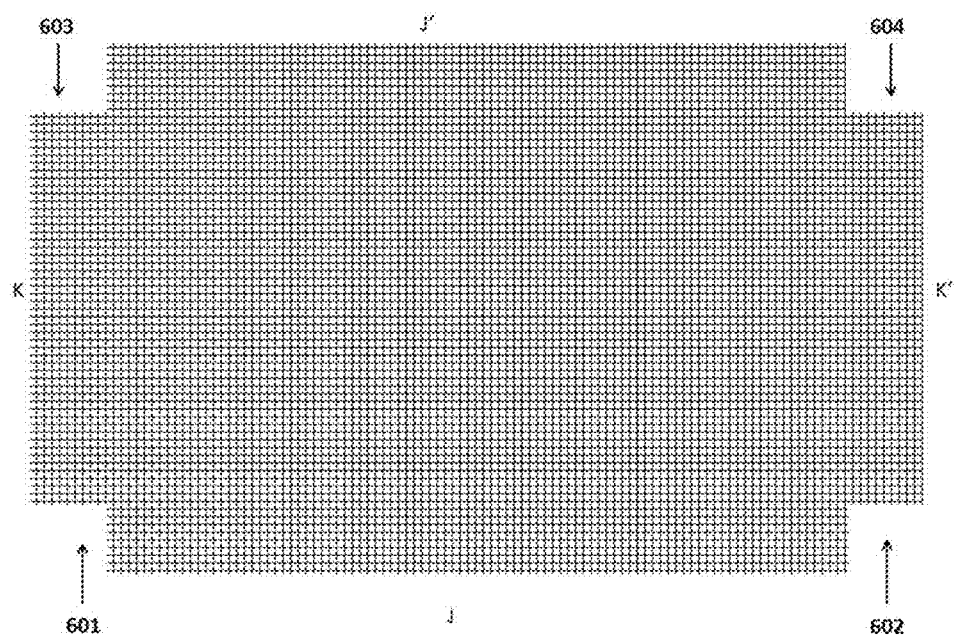

FIG. 22 is a view from the bottom of the package in the case of the second embodiment described by FIGS. 18 and 19 and the third embodiment described by FIGS. 20 and 21.

FIG. 23 A is a view of the package from the sides of the package J or J' as denoted in FIG. 22. FIG. 23 B is a view of the package from the sides of the package K or K' as denoted in FIG. 22.

FIG. 24 illustrates a typical transmission spectrum from the 4 output arms of a 1×4 MMI with a photonic crystal waveguide coupled microcavity in each arm.

Figure 25:
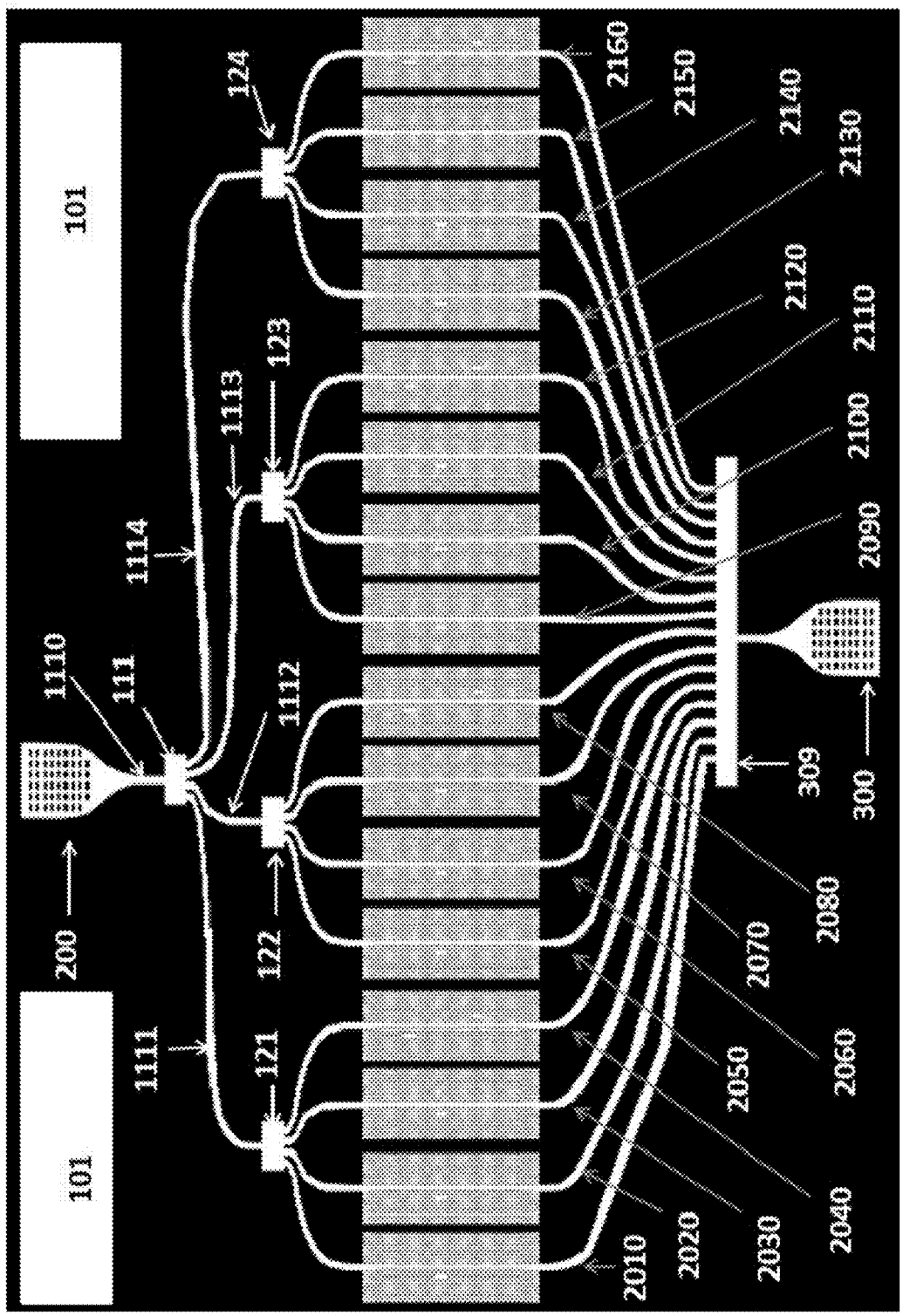

FIG. 25 describes one embodiment of the output waveguide configuration to output light using a single multimode interference power combiner.

Figure 26:
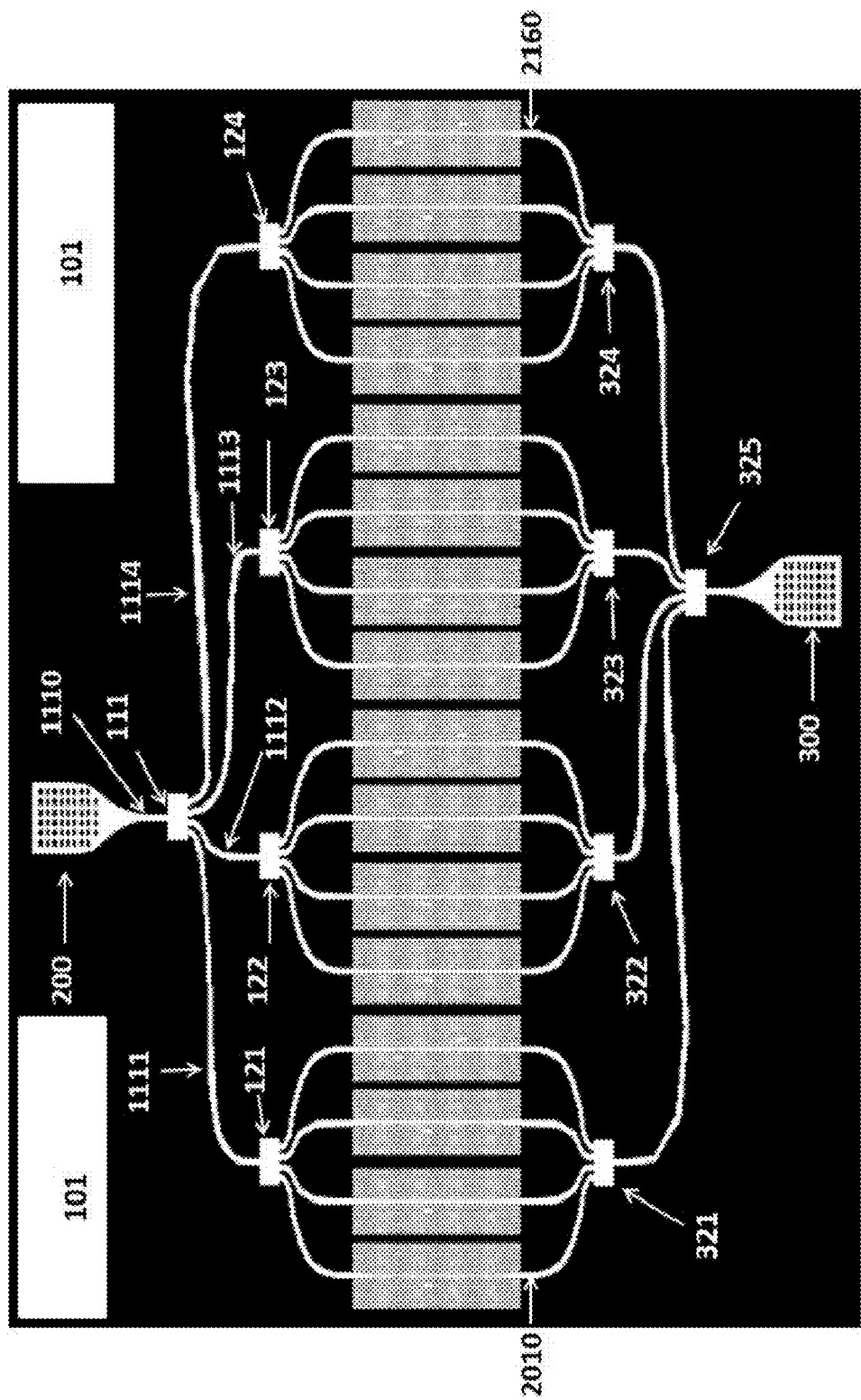

FIG. 26 describes one embodiment of the output waveguide configuration to output light using cascaded stages of multimode interference power combiners.

Figure 27:
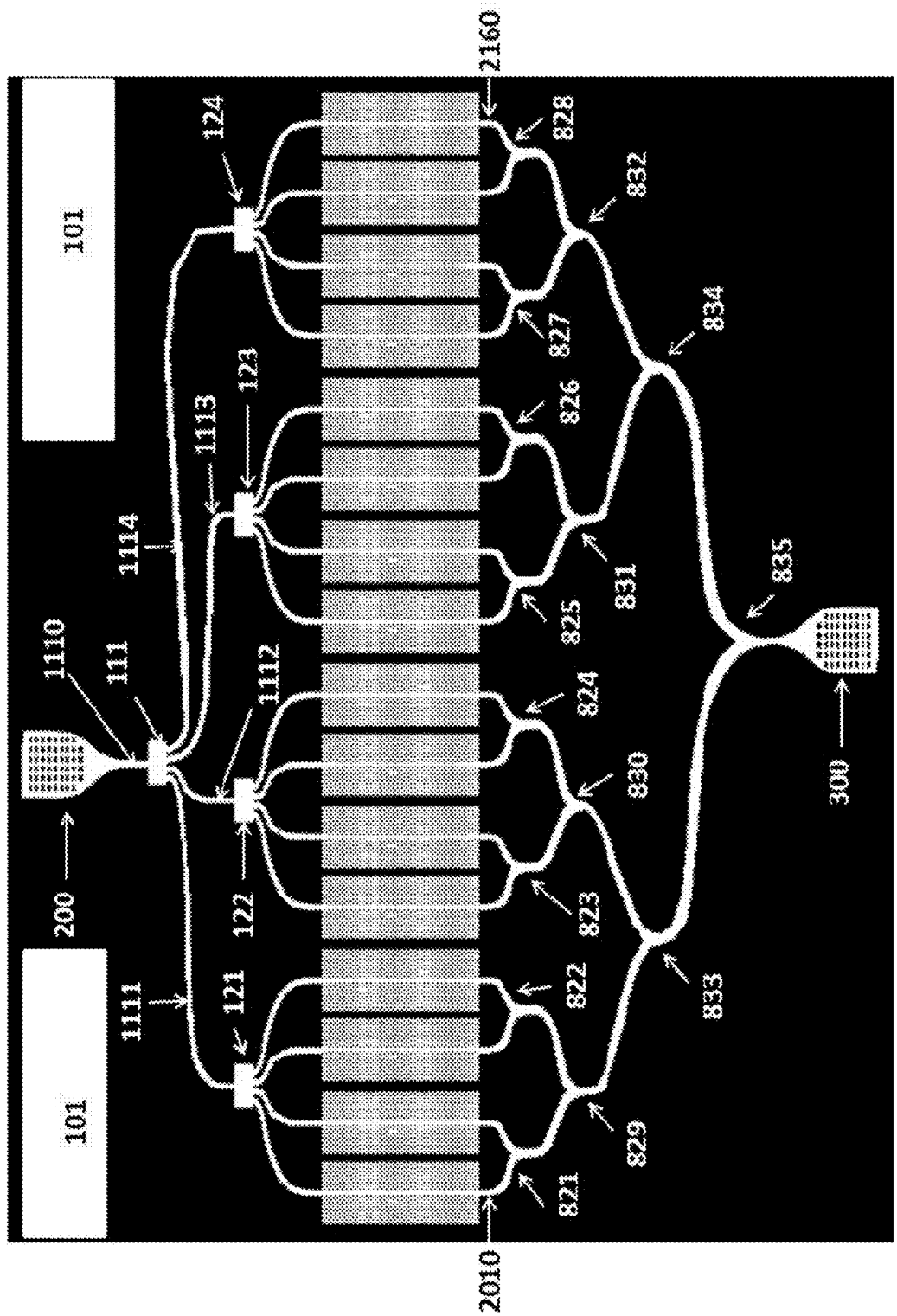

FIG. 27 describes one embodiment of the output waveguide configuration to output light using cascaded stages of Y-junction power combiners.

Figure 3:
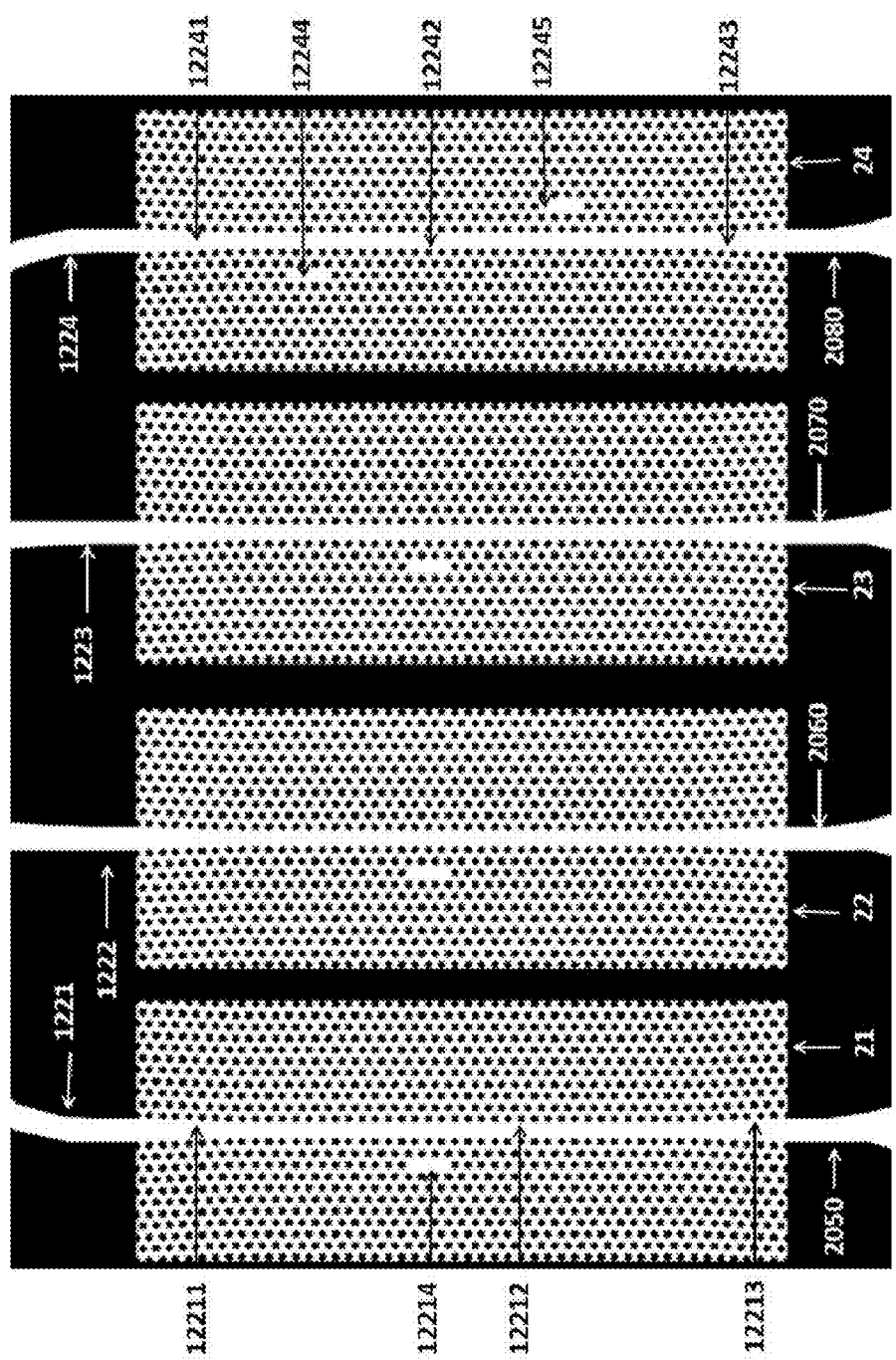
FIG. 3 is an enlarged top view of the photonic crystal waveguide section.
Figure 28A:
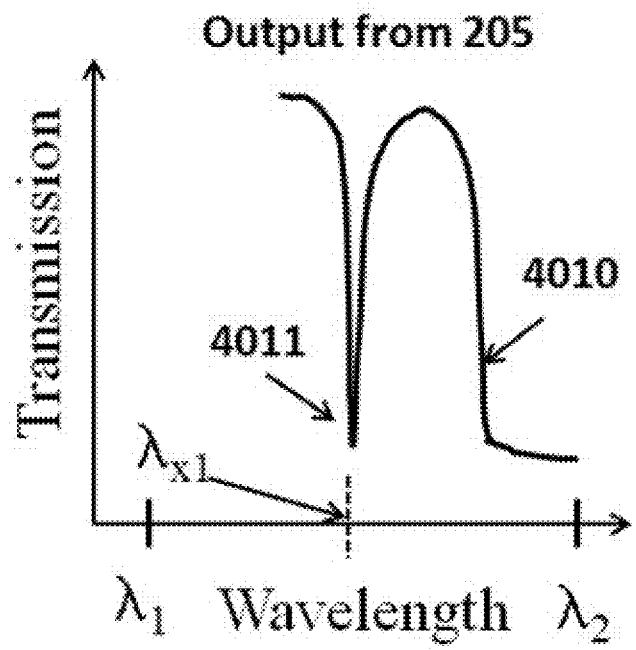
Figure 28B:
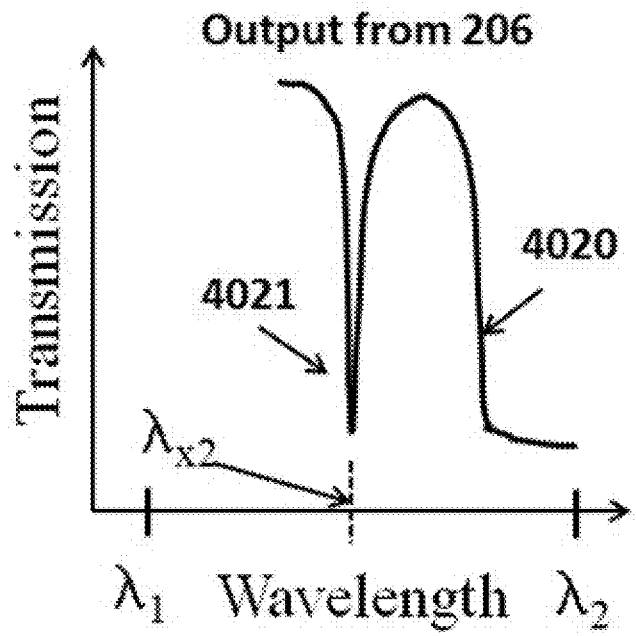
Figure 28C:
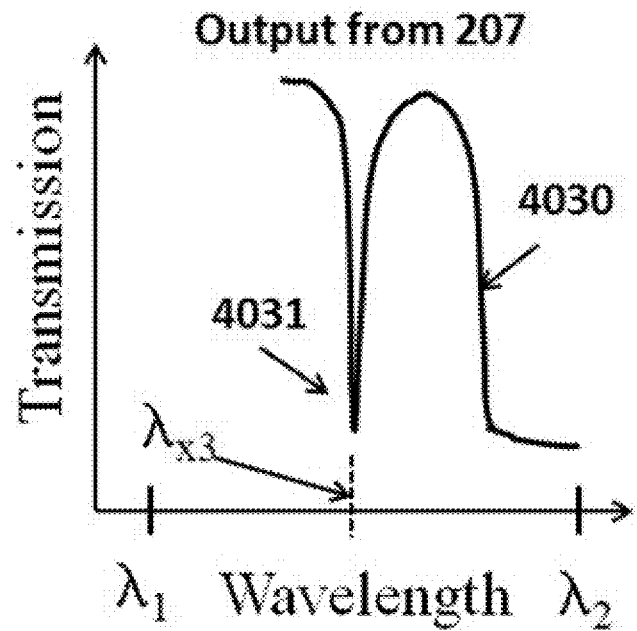
Figure 28D:
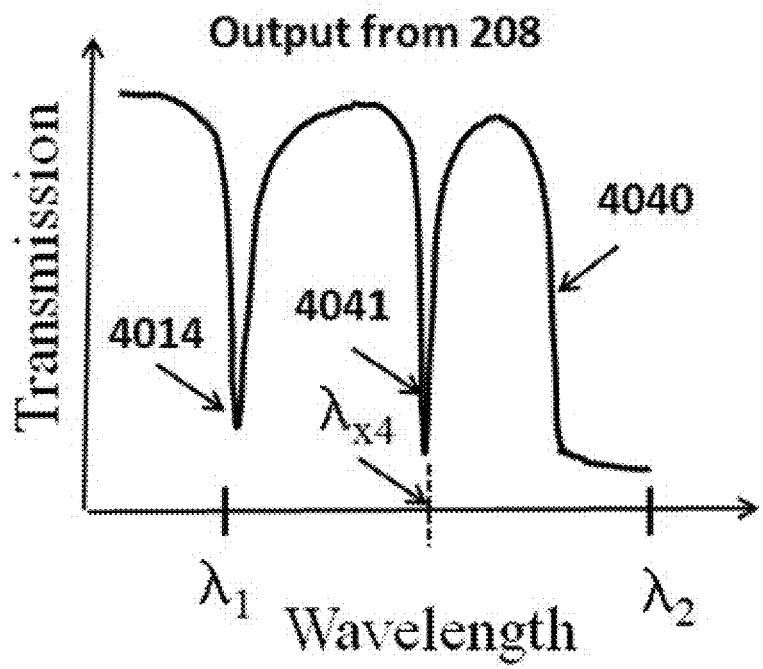
Figure 28E:
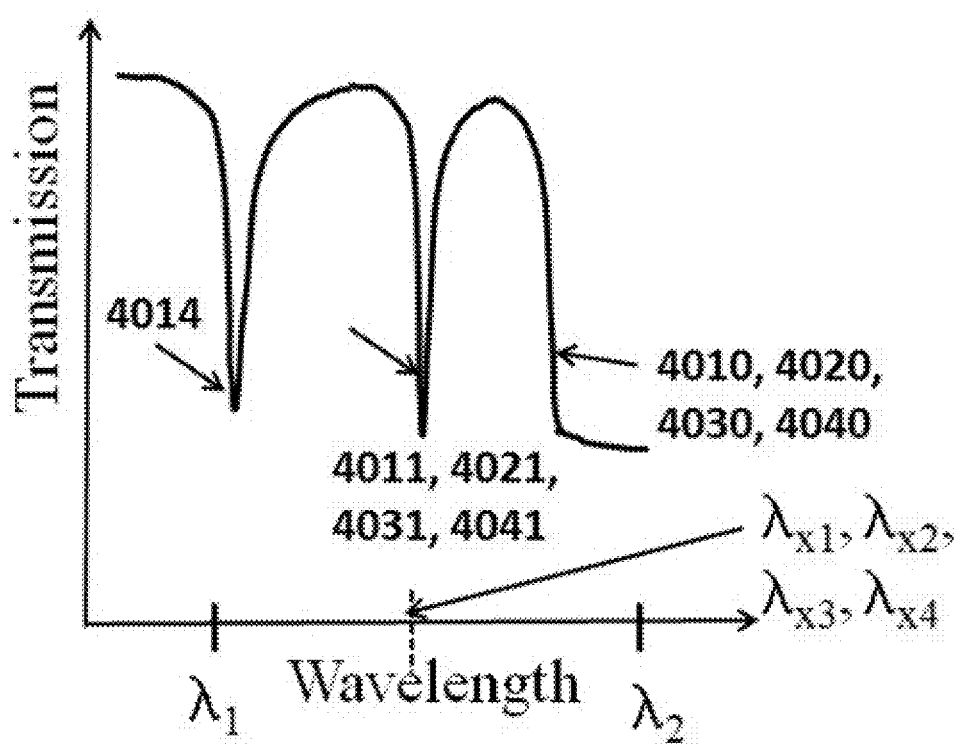

FIG. 28A, FIG. 28B, FIG. 28C, and FIG. 28D describe output optical transmission spectra observed at all output waveguides in FIG. 3, when the photonic crystal patterns in each arm have the same lattice constant and FIG. 28E describes the situation if the individual transmission spectra from FIG. 28A, FIG. 28B, FIG. 28C, and FIG. 28D were combined into a single output channel.

Figure 29A:
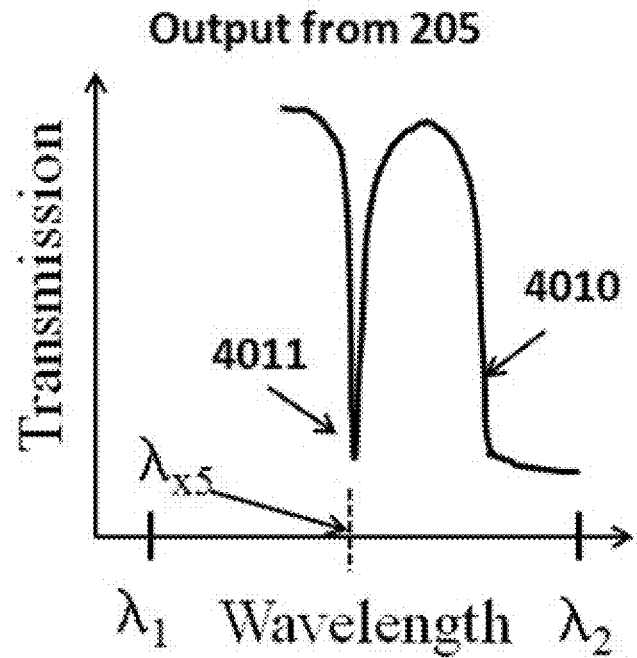
Figure 29B:
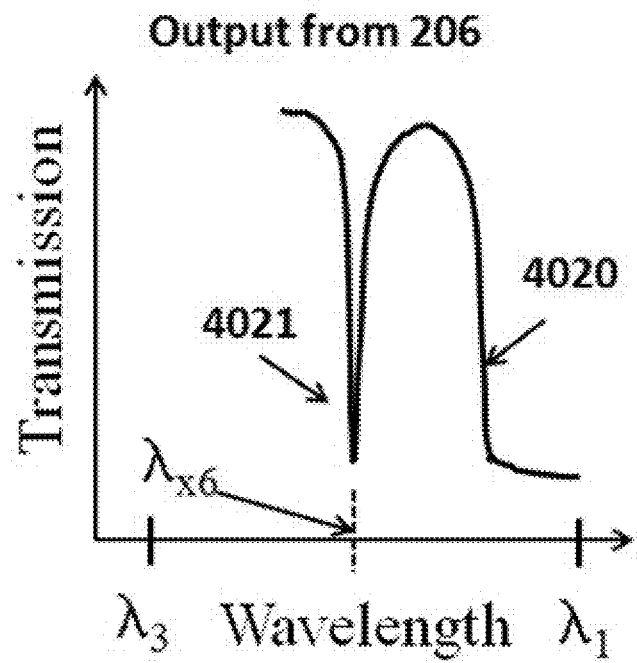
Figure 29C:
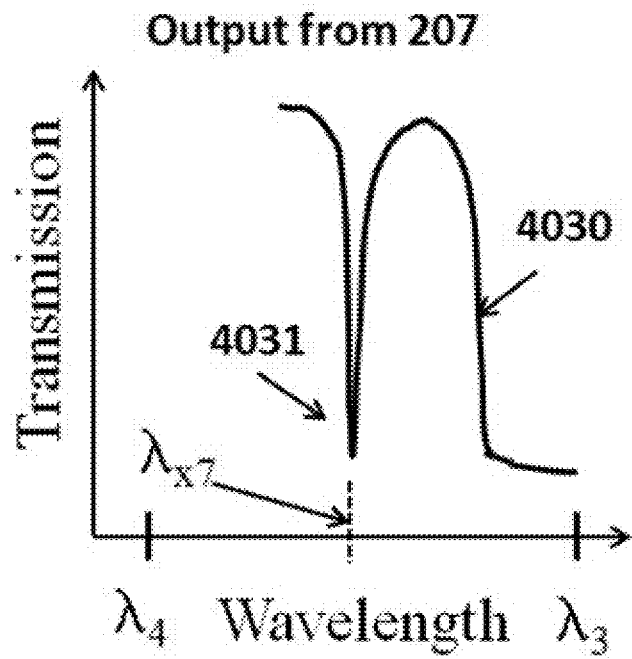
Figure 29D:
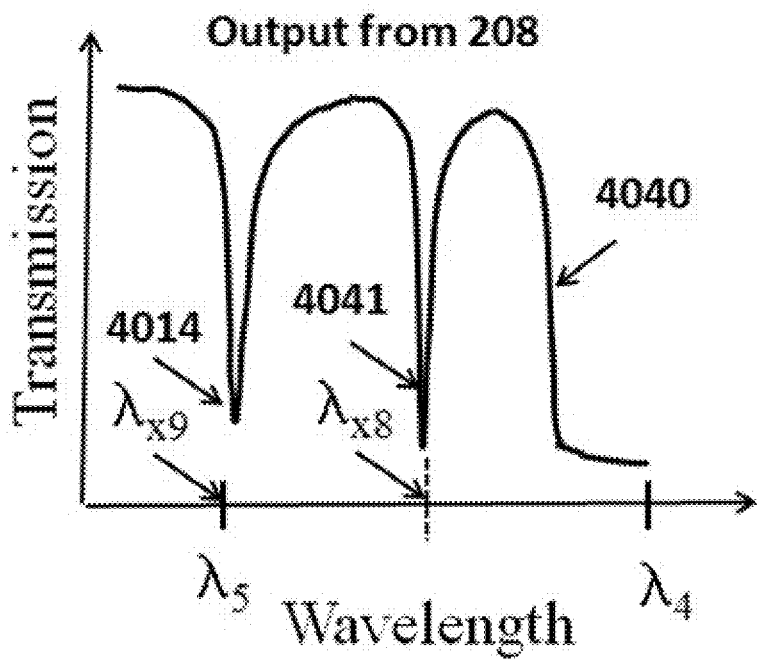
Figure 29E:
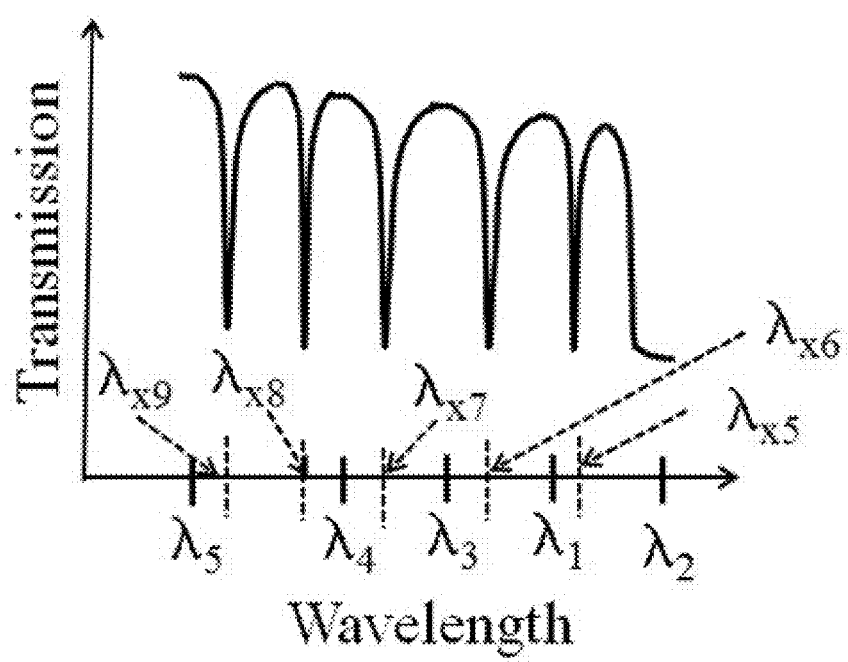

FIG. 29A, FIG. 29B, FIG. 29C, and FIG. 29D describe output optical transmission spectra observed at all output waveguides in FIG. 3, when the photonic crystal patterns in each arm have different lattice constants and FIG. 29E describes the situation if the individual transmission spectra from FIG. 29A, FIG. 29B, FIG. 29C, and FIG. 29D were combined into a single output channel.

Figure 30:
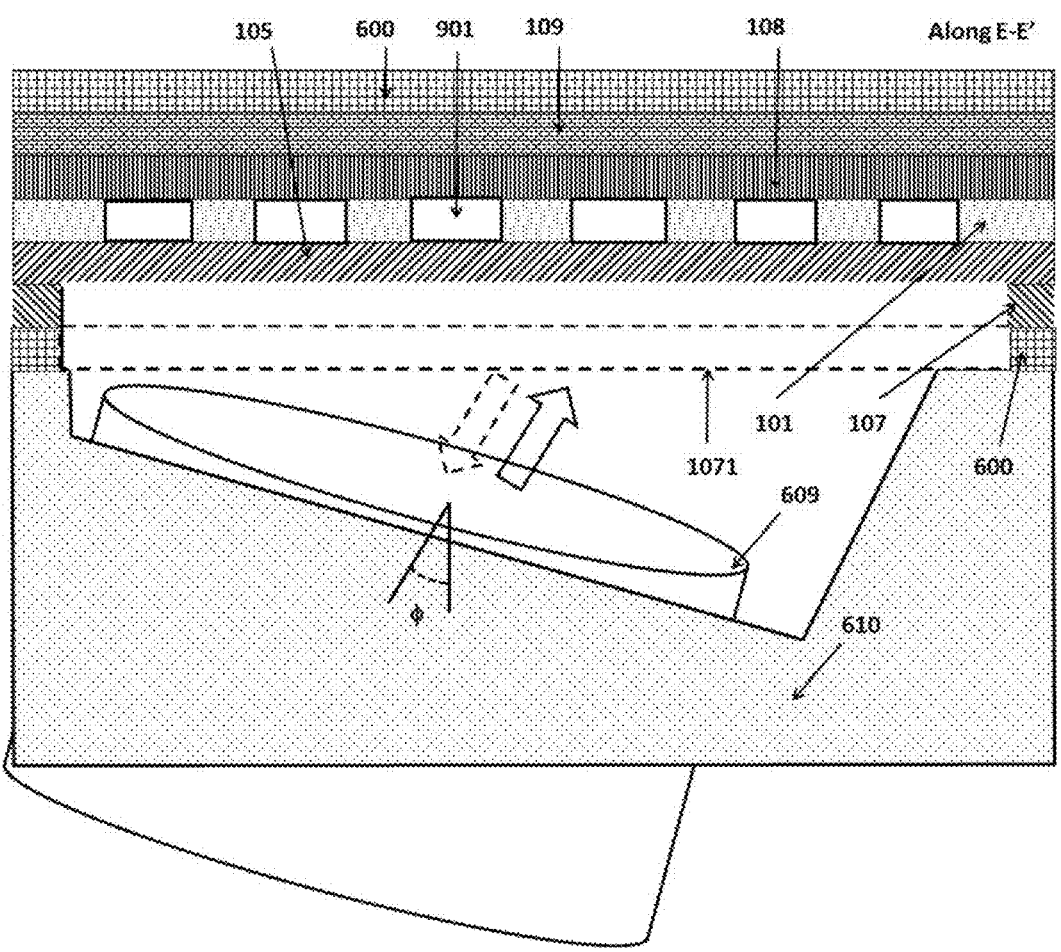

FIG. 30 describes the packaging of an external optical fiber with ultraviolet (UV)-cured epoxy to the packaged device.

Figure 31:
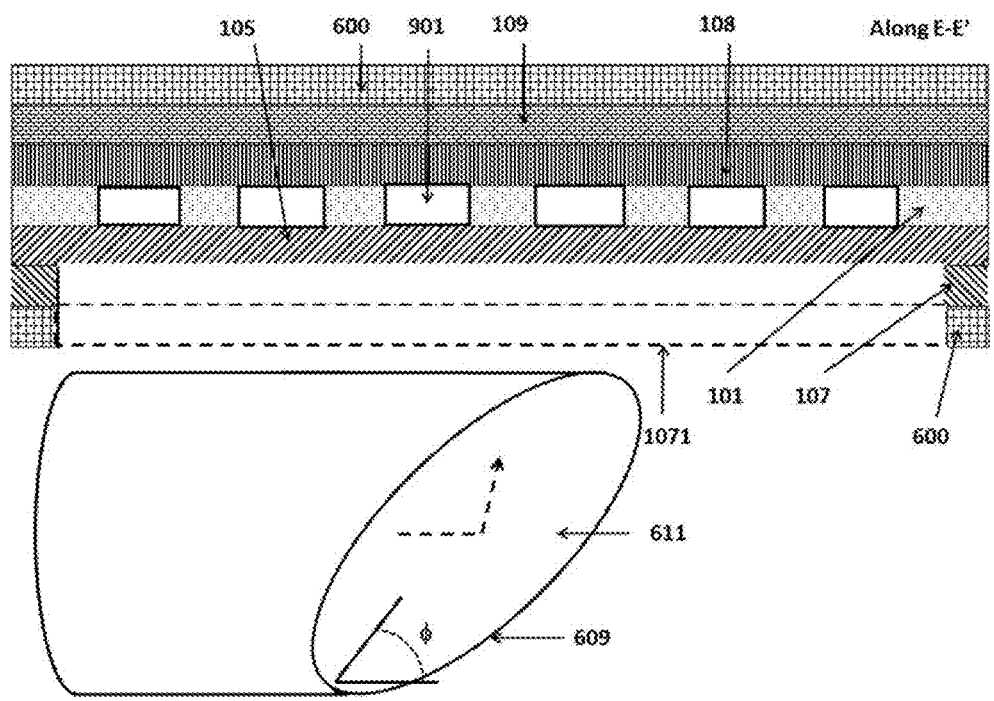

FIG. 31 describes the packaging of an external optical fiber with ultraviolet (UV)-cured epoxy to the packaged device when in addition the fiber facet is polished at an angle and coated with a reflecting material such as gold.

Figure 32:
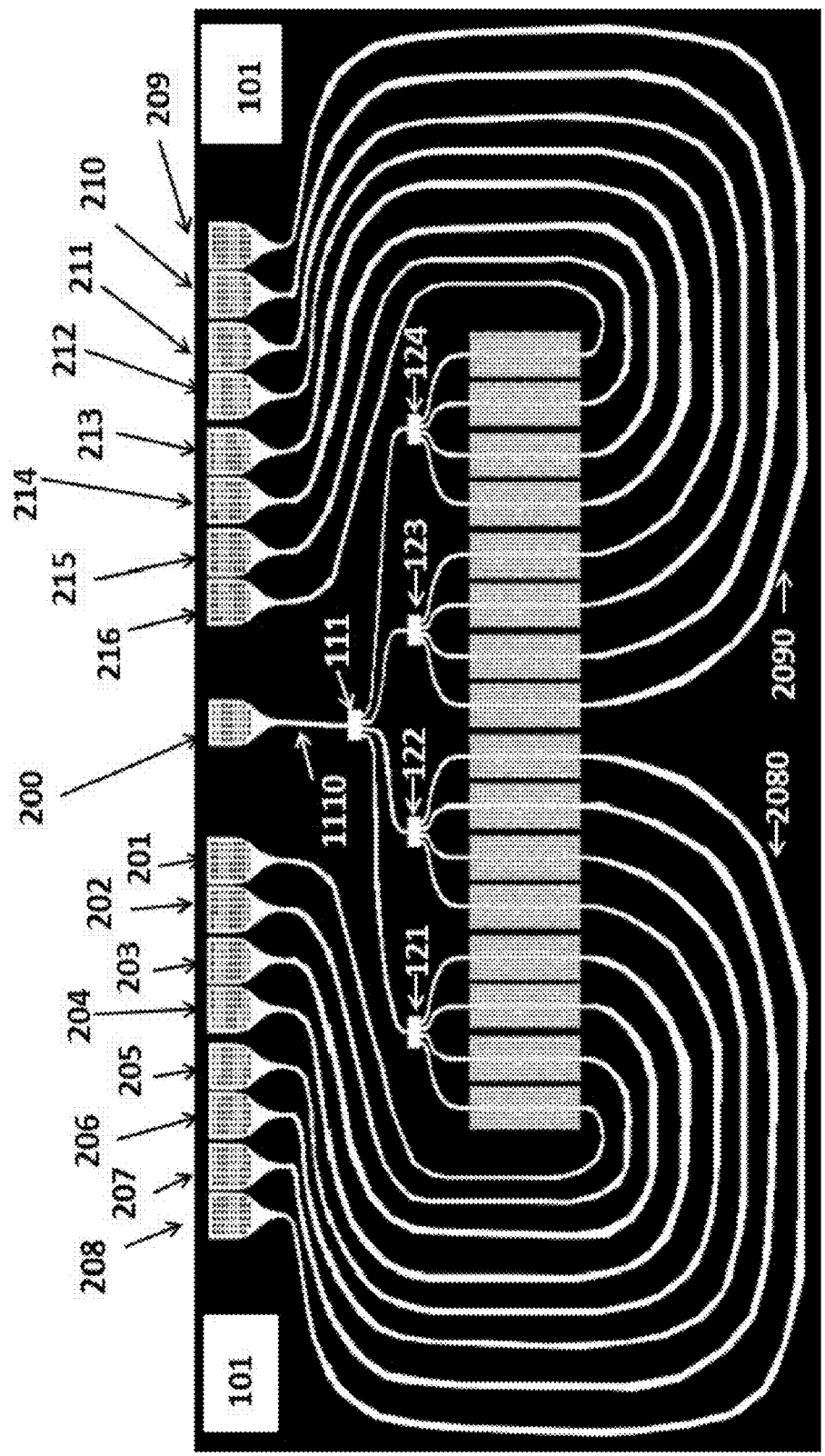

FIG. 32 describes one embodiment of the output waveguide configuration where the waveguides are bent by 180 degrees so that output sub-wavelength grating couplers are on the same side of the photonic crystal pattern as the input sub-wavelength grating coupler.

Figure 33A:
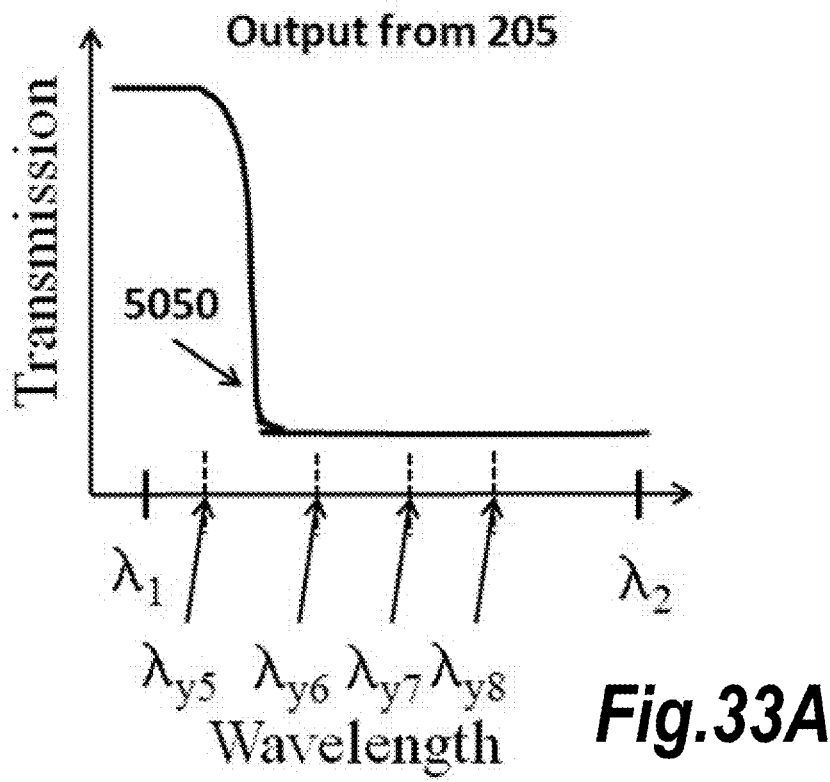
Figure 33B:
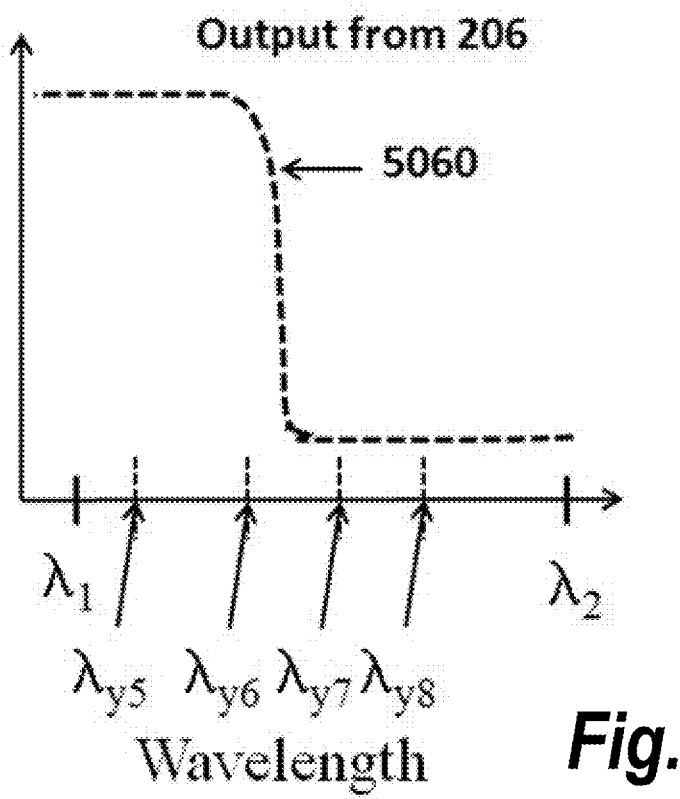
Figure 33C:
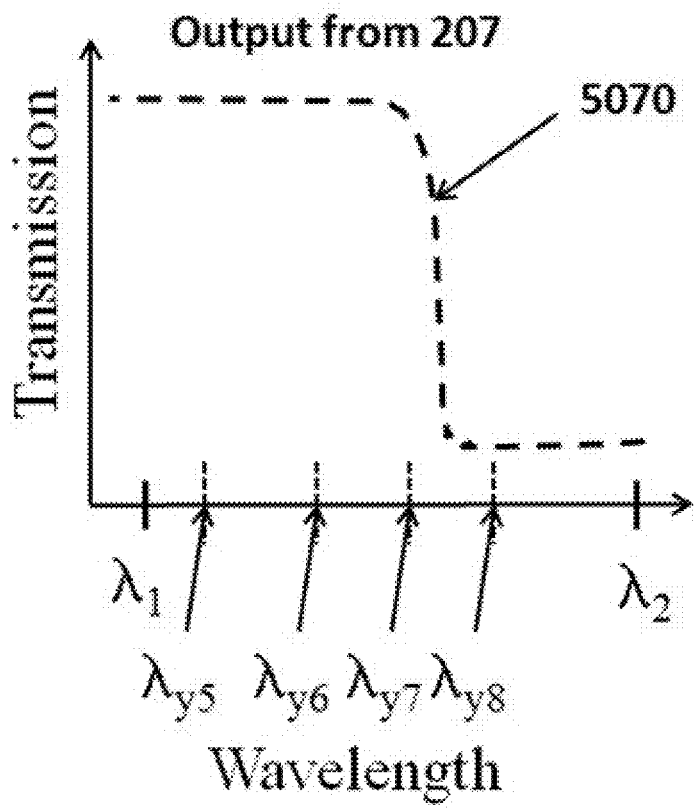
Figure 33D:
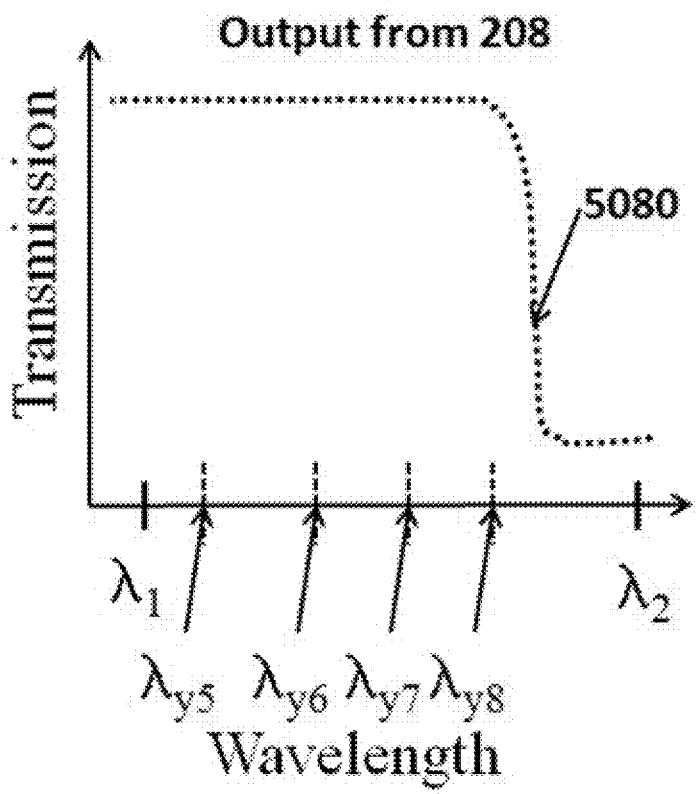
Figure 33E:
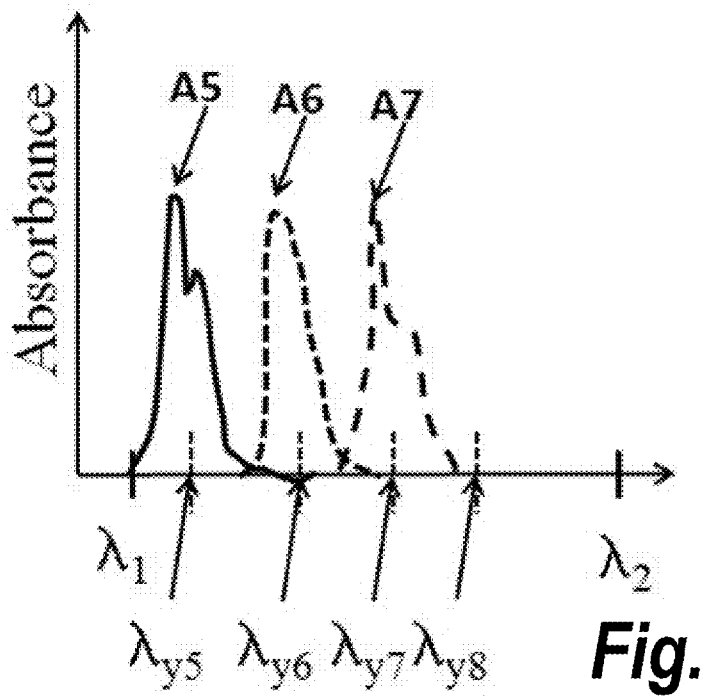
Figure 33F:
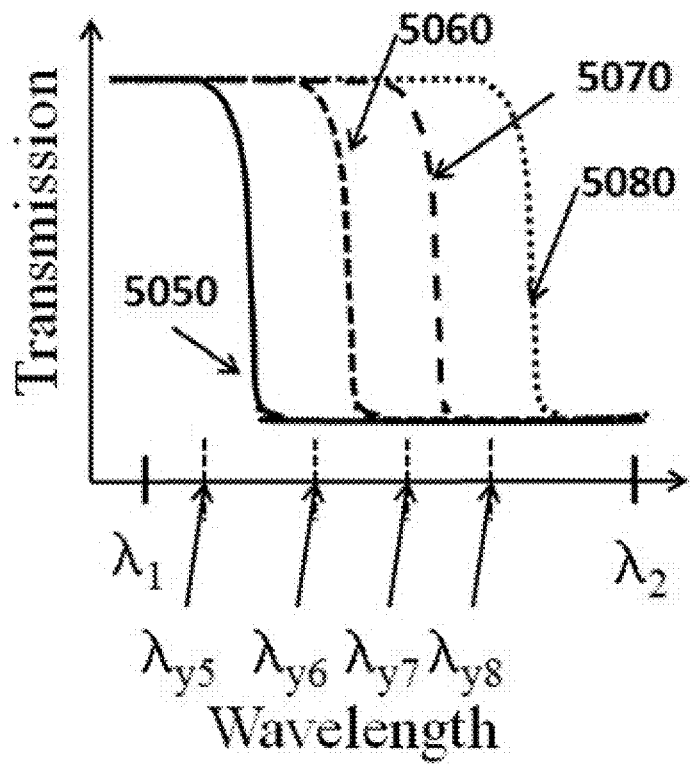

FIG. 33A, FIG. 33B, FIG. 33C, and FIG. 33D describe output optical transmission spectra observed at all output waveguides in FIG. 13, when the photonic crystal patterns in each arm have different lattice constants and FIG. 33F describes the situation if the individual transmission spectra from FIG. 33A, FIG. 33B, FIG. 33C, and FIG. 33D were combined into a single output channel. FIG. 33E shows typical absorption spectra of four unique analytes that are being detected by the four photonic crystal slot waveguides in each arm in FIG. 13.

V. DETAILED DESCRIPTION

Detailed Description of the Invention

In accordance with a preferred embodiment of the present invention, a device for multiplexing photonic crystal waveguide coupled microcavities comprises: a functional multimode interference power splitter that splits the input light equally into several output waveguides, a functional photonic crystal waveguide on each output arm of the MMI having a waveguide core along which light is guided, arrays of photonic crystal microcavities along the length of the photonic crystal waveguide each coated with a separate biomolecule specific to disease identification, an input and output photonic crystal impedance taper with gradually changed group index at the input and output end of the functional photonic crystal waveguide, which can bridge the refractive indices difference between conventional optical waveguides that form the output arms of the MMI and the functional photonic crystal waveguide. The sensor can be used to detect organic or inorganic substances such as proteins, DNA, RNA, small molecules, nucleic acids, virus, bacteria, cells, and genes, without requiring labels such as fluorescence or radiometry. Light (from a broadband source or LED) coupled into the MMI is split equally in the output arms of the MMI. On each output arm of the MMI, light couples into a photonic crystal waveguide that couples with the resonance of a photonic crystal microcavity and thereby drops the resonant wavelength in the microcavity, leading to a minimum in the transmission spectrum of the photonic crystal waveguide at the resonant wavelength. Transmission minima are observed for each resonant wavelength of the individual microcavities along the photonic crystal waveguide. The resonance wavelength shifts to longer wavelengths in response to the attachment of a material on the microcavity surface leading to the corresponding shift of the transmission minimum of that microcavity.

In another embodiment of the present invention, a device for multiplexing photonic crystal waveguide coupled microcavities comprises: a functional MMI that splits the input light equally into several output waveguides, a functional photonic crystal waveguide on each output arm of the MMI having a waveguide core along which light is guided, arrays of photonic crystal microcavities along the length of the photonic crystal waveguide each coated with a separate polymer or hydrogel specific to a unique environmental parameter, an input and output photonic crystal impedance taper with gradually changed group index at the input and output end of the functional photonic crystal waveguide, which can bridge the refractive indices difference between conventional optical waveguides and the functional photonic crystal waveguide. The sensor can be used to detect changes in temperature, pressure, humidity, molarity of solution, acidity or alkalinity (pH) of aqueous medium, ion concentration of solutions, trace gases in the atmosphere, pollutants in ground water that can be organic or inorganic, volatile and non-volatile, pesticides and thereof in a single optical transmission measurement. A unique polymer or hydrogel is chosen with maximum response to changes in each of the above parameters and a unique microcavity along the waveguide is coated with a unique polymer or hydrogel. The polymer may be an ion-sensitive electrode or optode for the detection of ions in solution. Light (from a broadband source or LED) coupled into the MMI is split equally in the output arms of the MMI. On each output arm of the MMI, light couples into a photonic crystal waveguide that couples with the resonance of a photonic crystal microcavity and thereby drops the resonant wavelength in the microcavity, leading to a minimum in the transmission spectrum of the photonic crystal waveguide at the resonant wavelength. Transmission minima are observed for each resonant wavelength of the individual microcavities along the photonic crystal waveguide, in the pristine condition. The resonance wavelength shifts to longer wavelengths in response to changes in ambient parameters listed above leading to the corresponding shift of the transmission minimum of that microcavity, the amount of transmission minimum shift determines the absolute change in ambient conditions in the vicinity of the microarray device.

In another embodiment of the present invention, a device for multiplexing photonic crystal slot waveguides comprises: a functional MMI that splits the input light equally into several output waveguides, a functional photonic crystal slot waveguide on each output arm of the MMI having a waveguide core along which light is guided, an input and output photonic crystal impedance taper with gradually changed group index at the input and output end of the functional photonic crystal waveguide, which can bridge the refractive indices difference between conventional optical waveguides and the functional photonic crystal waveguide, the one or more slots in the photonic crystal waveguide extending in the input impedance taper, output impedance taper, input ridge waveguide and output ridge waveguide. The top cladding is a layer of organic polymer such as PDMS (poly-dimethyl-siloxane) or PMMA (poly-methyl methyl-acrylate) that is hydrophobic but readily swells in the presence of volatile organic compounds such as benzene, toluene, xylene, or ethylbenzene. The polymer which forms the top cladding also fills the photonic crystal holes as well as the slot in the middle of the photonic crystal slot waveguide. Light (from a broadband source or LED) coupled into the multimode interference (MMI) power splitter is split equally in the output arms of the MMI. On each output arm of the MMI, light couples into a photonic crystal slot waveguide, and in the presence of the analyte, has enhanced absorption by the analyte due to the increase in the effective optical path length caused by the enhanced field intensity in the slot and the slowdown effect of photonic crystal waveguide dispersion. Due to the water filtering capability of the hydrophobic polymer, only the volatile organic compound contaminants in the water are absorbed by the polymer; light is guided in the photonic crystal slot waveguide and transmission spectra are measured without interference from the strong absorption signatures of water. Transmission spectra are measured covering the entire transmission bandwidth of the photonic crystal slot waveguide, both in the presence and absence of the analyte, in this case the volatile organic compounds, in the water. The presence of the analyte leads to a decrease in transmission intensity due to absorption, compared to the transmission in the absence of the analyte. Absorbance spectrum of the analyte is determined from the difference in transmission, without interference of the water medium in which the analyte of interest is located.

For the measurement of environmental parameters in situ, the device is incorporated with a filter to remove macroscopic dirt and dust particles. The filter can be a macroscopic filter incorporated off-chip or a microfluidic filter incorporated on-chip.

Methods for fabricating photonic crystal structures are widely described in the literature. Sensor structures of the invention have higher sensitivity than previous structures due to the use of two-dimensional photonic crystal microcavities with resonances that have high quality factor together with the slow light effect of two-dimensional photonic crystal waveguides Ink-Jet printing is used for patterning of multiple biomolecules exclusively on photonic crystal microcavities that preserves biomolecule functionality in aqueous phase.

Detailed descriptions of the preferred embodiments are provided herein. It is to be understood, however, that the present invention may be embodied in various forms. Therefore, specific details disclosed herein are not to be interpreted as limiting, but rather as a basis for the claims and as representative basis for teaching one skilled in the art to employ the present invention in virtually any appropriately detailed system, structure or manner.

Figure 1:
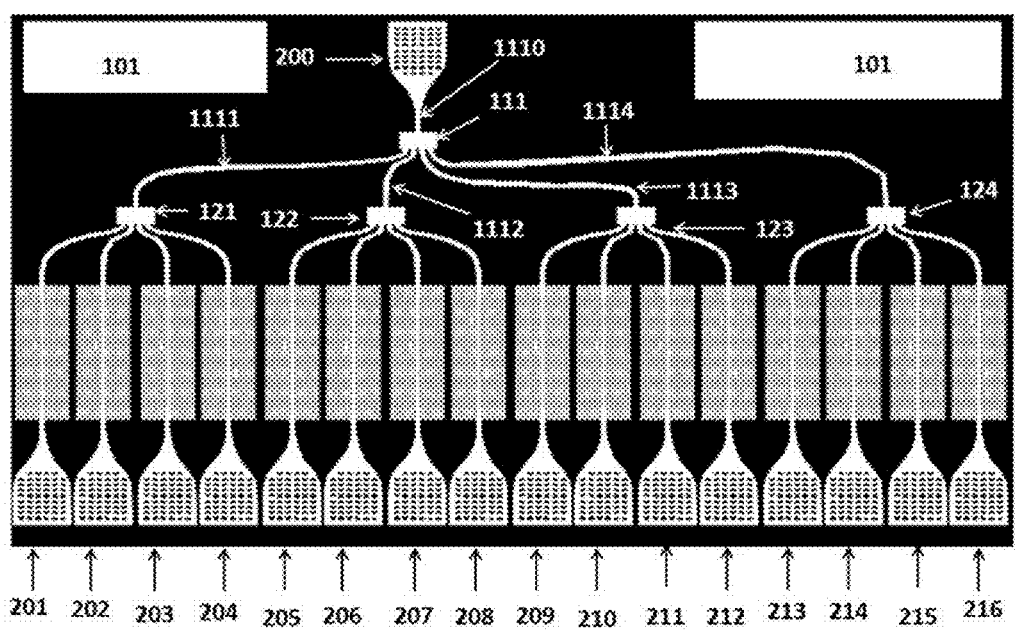

FIG. 1 presents a top view schematic drawing of a multiplexed photonic crystal waveguide device. It consists of a functional MMI 111 with one input arm 1110 which is a ridge waveguide and 4 representative output arms 1111, 1112, 1113, and 1114 which are four ridge waveguides. On each output arm 1111, 1112, 1113, and 1114, the second stage of a functional MMI is made. One skilled in the art will note that the number of output arms, shown as four in the figure can actually be any number m=1, 2, 3, 4, 5 . . . M. A representative second stage MMI on the arm 1112 is denoted as 122. The MMI 122 has four output arms 1221, 1222, 1223, and 1224 which are four ridge waveguides. Elements 1221, 1222, 1223, and 1224 have been shown in detail in FIG. 2 to avoid cluttering in FIG. 1. Only two MMI stages are shown here, but one skilled in the art will note that the number of cascaded MMI stages can be cascaded n times where n=1, 2 . . . N. Each output arm 1221, 1222, 1223, and 1224 is a ridge waveguide that terminates in functional photonic crystal patterned regions 21, 22, 23, and 24 respectively. Elements 21, 22, 23, and 24 have been shown in detail in FIG. 2 and FIG. 3 to avoid cluttering in FIG. 1. The core of the photonic crystal patterned region 21 comprises a functional photonic crystal waveguide 12212, an input impedance taper 12211 between the input ridge waveguide 1221 and the photonic crystal waveguide 12212 and an output impedance taper 12213 between the output ridge waveguide 2050 and the photonic crystal waveguide 12212. Only one photonic crystal microcavity 12214 is shown arrayed along the length of the photonic crystal waveguide 12212 for clarity. Elements 12211, 12212, 12213, and 12214 have been shown in detail in FIG. 3 to avoid cluttering in FIG. 1. In general, P photonic crystal microcavities can be arrayed along the length of the single photonic crystal waveguide 12212. For instance, two photonic crystal microcavities 12244 and 12245 are arrayed along the length of the functional photonic crystal waveguide 12242 in the photonic crystal patterned region 24. Elements 12241, 12242, 12243, 12244, and 12245 have been shown in detail in FIG. 3 to avoid cluttering in FIG. 1. The photonic crystal patterned regions 21, 22, 23, and 24 include a number of column members 102 etched through or partially into the semiconductor slab 101. Within each photonic crystal patterned region, the waveguide core 141 is defined as the space between the centers of two column members adjacent to the region where the columns are absent. In one preferred embodiment, the column members 102 are arranged to form a periodic lattice with a lattice constant α. In some embodiments, the width of waveguide core 141 can range from 0.5 times sqrt(3) times the lattice constant or period α to 50 times sqrt(3) times the lattice constant or period α. In the figure, the photonic crystal microcavities are parallel to the photonic crystal waveguide and are placed 2 lattice periods away from the waveguide. The core is shown in detail in FIG. 4.

Light is coupled into the input arm 1110 of the MMI 111 via a sub-wavelength grating coupler 200. The output light from each output ridge waveguide, in one instance, the output ridge waveguide 2050 is coupled out of the plane of the slab 101 by an output sub-wavelength grating coupler 205. Sub-wavelength grating couplers 201, 202, 203 . . . 216 couple light out from the output ridge waveguides 2010, 2020, 2030 . . . 2160 respectively out of the plane of the slab 101. The light output from the individual sub-wavelength grating couplers 201, 202, 203 . . . 216 can be detected by individual external detectors or individual external optical fibers, one each for each output sub-wavelength grating coupler 201, 202, 203 . . . 216. The light output from the all individual sub-wavelength grating couplers 201, 202, 203 . . . 216 can also be detected at the same time by a single individual external detector or a single external optical fibers.

All white structures in FIG. 1 are part of the semiconductor slab 101 and all black areas in FIG. 1 are voids formed by etching the corresponding features as defined by the black areas, into the slab 101 either completely or partially through the slab.

Figure 2:
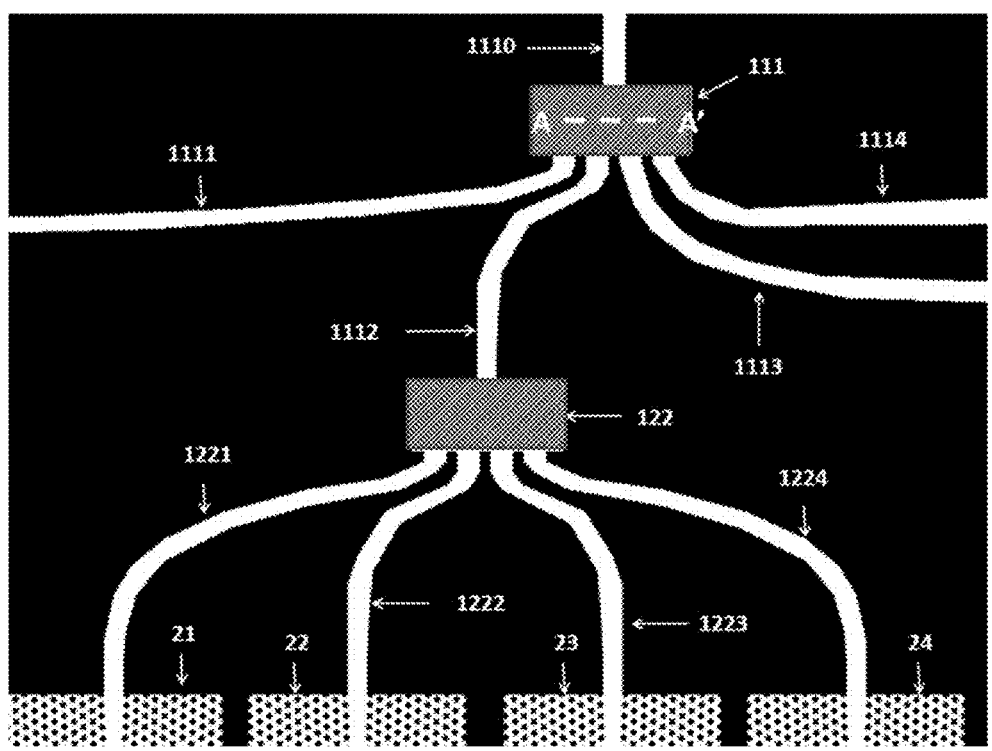
FIG. 2 is an enlarged schematic top view of a section of the cascaded MMI.

FIG. 2 is an enlarged top view of the input section in FIG. 1 showing the first stage MMI 111 and one of the four second stage MMIs 122. The functional MMI 111 has one input arm 1110 and 4 output arms 1111, 1112, 1113, and 1114 which are four ridge waveguides. One skilled in the art will note that the number of output arms, shown as four in the figure can actually be any number m=1, 2, 3, 4, 5 . . . M. The output ridge waveguide 1112 of the first stage MMI 111 forms the input to the second stage MMI 122. The MMI 122 has four output arms 1221, 1222, 1223, and 1224 which are four ridge waveguides. Each ridge waveguide 1221, 1222, 1223, and 1224 terminates in functional photonic crystal patterned regions 21, 22, 23, and 24 respectively.

FIG. 3 is an enlarged top view of the photonic crystal patterned regions 21, 22, 23, and 24 respectively at the termination of the ridge waveguides 1221, 1222, 1223, and 1224. The core of the photonic crystal patterned region 21 comprises a functional photonic crystal waveguide 12212, an input impedance taper 12211 in the input end of the photonic crystal waveguide between the input ridge waveguide 1221 and the photonic crystal waveguide 12212 and an output impedance taper 12213 at the output end of the photonic crystal waveguide between the output ridge waveguide 2050 and the photonic crystal waveguide 12212. Only one photonic crystal microcavity 12214 is shown arrayed along the length of the photonic crystal waveguide 12212 for clarity. In general, p=1, 2, 3 . . . P photonic crystal microcavities can be arrayed along the length of the single photonic crystal waveguide 12212. For instance, two photonic crystal microcavities 12244 and 12245 are arrayed along the length of the functional photonic crystal waveguide 12242 in the photonic crystal patterned region 24.

Between the ridge waveguide 1221 and the photonic crystal waveguide 12212, at the input end of the photonic crystal waveguide, there is an impedance taper 12211 for coupling of light from ridge waveguide to photonic crystal waveguide with high efficiency. Similarly, between the photonic crystal waveguide 12212 and the output ridge waveguide 2050, at the output end of the photonic crystal waveguide, there is another impedance taper 12213 for better coupling efficiency. The waveguides are tapered by shifting the columnar members by x times α in the direction perpendicular to 12212, in the plane of the waveguide, where α is the lattice constant and x varies from 0.01 to 0.1 in steps of 0.01, from photonic crystal waveguide to ridge waveguide. Optical confinement of light that propagates in the core in the photonic crystal patterned region comprising the functional photonic crystal waveguide 12212, input and output impedance tapers 12211 and 12213, respectively, is achieved in the horizontal plane of the slab, parallel to the plane of the substrate, by the periodic lattice structure of the photonic crystal patterned region 21 with two-dimensional periodicity. Optical confinement in the direction out of the plane of the slab is achieved by total internal reflection between the high index slab material in the core and the lower refractive indices of the top cladding 106 and bottom cladding 105, relative to the slab 101.

Figure 4:
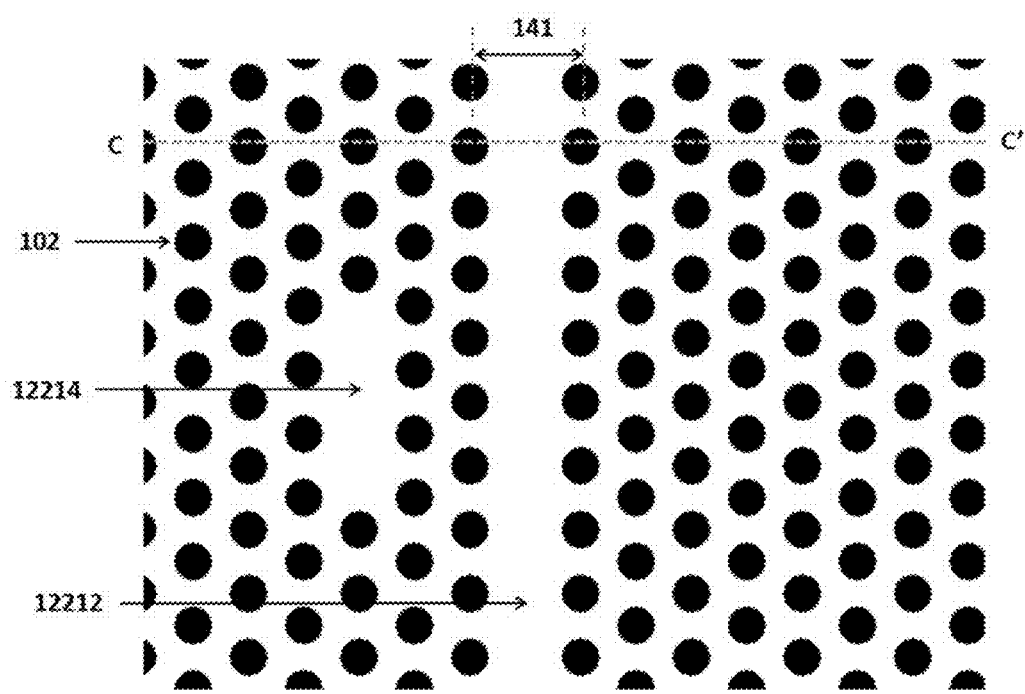
FIG. 4 is an enlarged top view showing the photonic crystal microcavity coupled to the photonic crystal waveguide.

FIG. 4 is an enlarged top view of a section of the photonic crystal patterned region 21 showing the functional photonic crystal microcavity 12214 coupled to the functional photonic crystal waveguide 12212. The columnar members 102 etched into the slab are also shown. The photonic crystal waveguide 12212 is defined by filling a complete row of columnar members with the semiconductor slab material 101. Similarly, a photonic crystal microcavity, for instance 12214, is defined by filing a row of 3 columnar members 102 with semiconductor material 101. One skilled in the art will notice that the photonic crystal microcavity 12214 can have different geometries as described in the literature. The core 141 is the region through which the light propagates in the photonic crystal waveguide.

Figure 5:
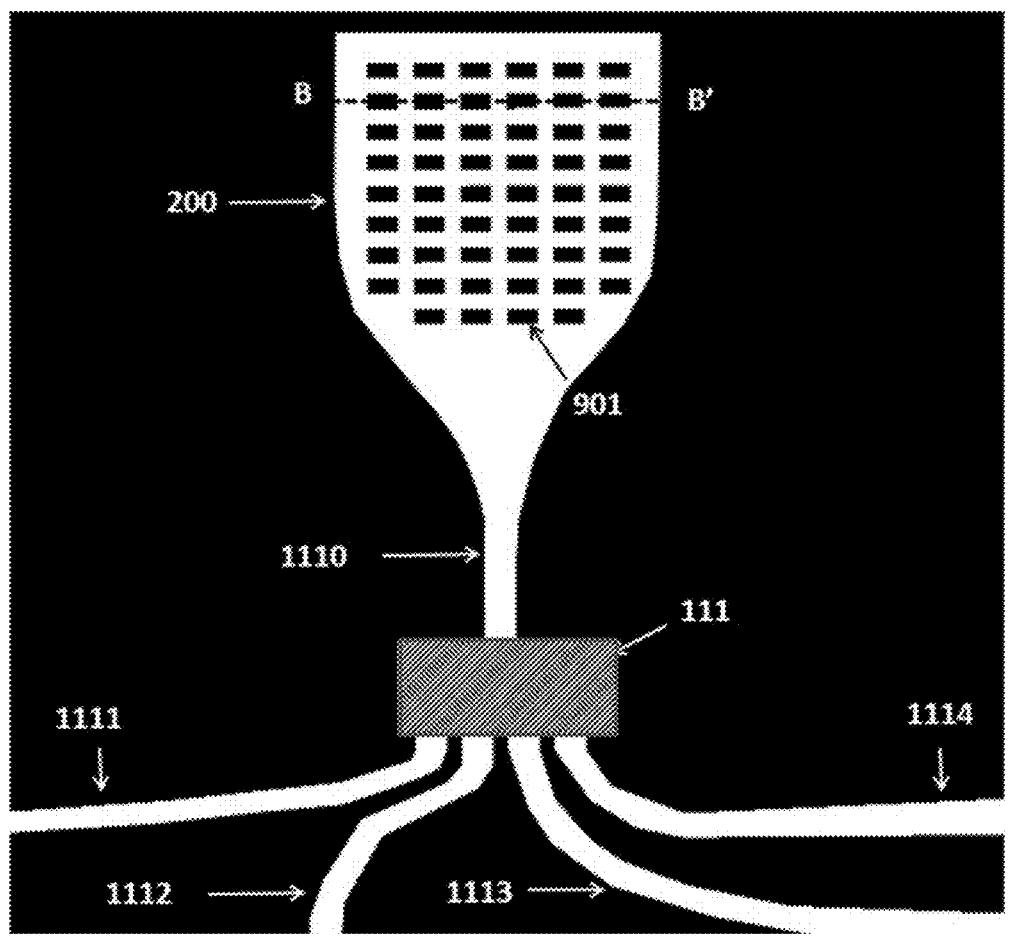
FIG. 5 is an enlarged top view of the input sub-wavelength grating coupler that inputs light to the first cascaded stage of the MMI.

FIG. 5 is an enlarged top view of the input sub-wavelength grating coupler 200 defined in the semiconductor slab 101. Rectangular voids 901 are etched into the region 200 in the form of a rectangular array. Input ridge waveguide 1110, the first stage MMI 111, and the corresponding output ridge waveguides from the MMI, which are 1111, 1112, 1113, and 1114 respectively are also shown.

Figure 6:
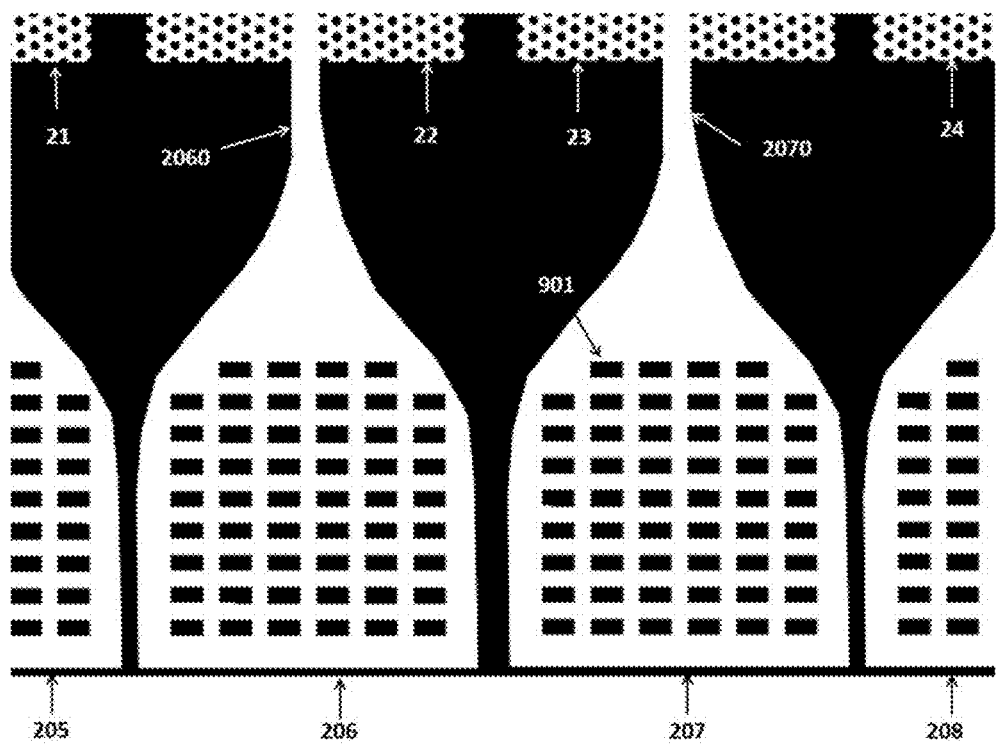
FIG. 6 is an enlarged top view of the output sub-wavelength grating couplers.

FIG. 6 is an enlarged top view of the output sub-wavelength grating couplers 205, 206, 207, and 208 defined in the semiconductor slab 101. The elements 205, 206, 207, and 208 are at the output end of the ridge waveguides 2050, 2060, 2070, and 2080 respectively. The ridge waveguides 2050, 2060, 2070, and 2080 originate from the photonic crystal patterned regions 21, 22, 23, and 24 respectively. Rectangular voids 901 are etched into the regions 205, 206, 207, and 208 in the form of a rectangular array.

Figure 7:
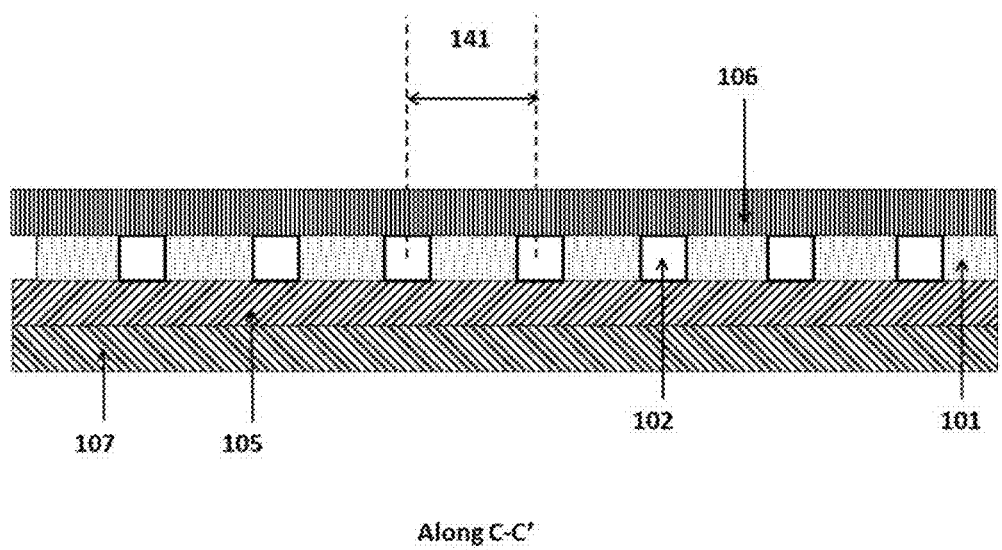
FIG. 7 is a cross-sectional view of the device in FIG. 4 along the plane C-C'.

FIG. 7 is a schematic cross-section of FIG. 4 taken along the plane C-C' in the photonic crystal patterned region. FIG. 7 shows the substrate 107, the bottom cladding 105 disposed on the substrate, the semiconductor slab 101 disposed on the bottom cladding with columnar members 102 etched through the slab. In one embodiment, the top cladding 106 is air. When analytes are introduced in solution on top of the device, the analyte medium forms the top cladding 106. However, one skilled in the art will note that the top cladding can be any organic or inorganic dielectric material, columnar members 102 can extend through 101 as well as through the bottom cladding 105 to reach the substrate 107. The material of the top cladding 106 can fill the columnar members 102 either fully or partially during device operation. Although the structure within the slab 101 is substantially uniform in the vertical direction in this embodiment, one skilled in the art will understand that vertically non-uniform structure, such as the columnar members 102 whose radii are varying along the vertical direction, may be used as well. The column members 102 can be either simply void or filled with other dielectric materials.

Figure 8:
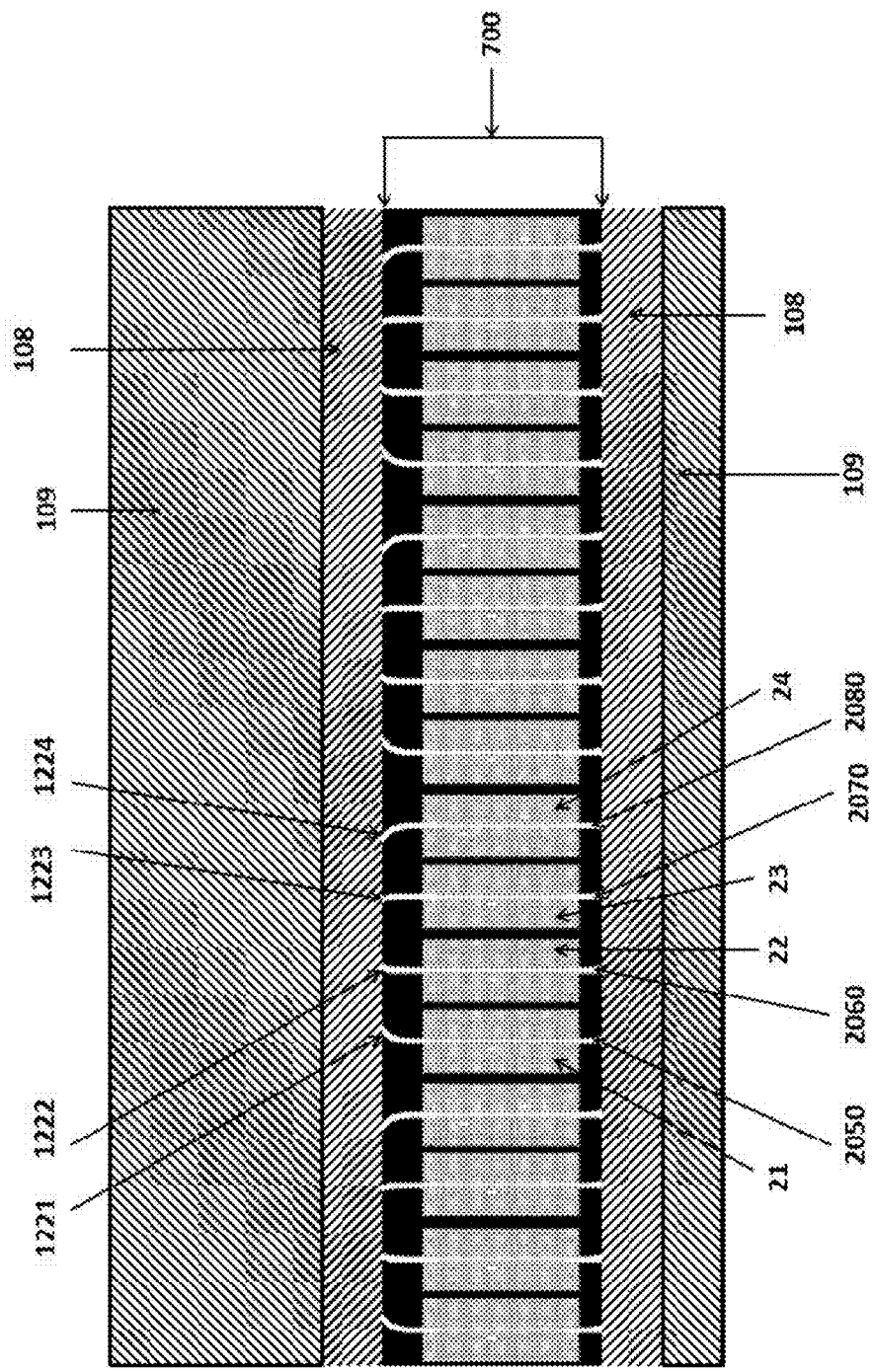
FIG. 8 is a top view of the device in FIG. 1 together with the top layer cover polymer and rigid dielectric cover to form a microfluidic channel.

In FIG. 8, which is a top view, the MMIs of all the cascaded stages and the input and output sub-wavelength grating couplers that were shown in FIG. 1, are covered with a cover polymer 108. The region 700 is kept free from any cover polymer and forms a microfluidic channel. A rigid dielectric cover 109 is put on top of the cover polymer as shown. In some embodiments, the rigid dielectric cover 109 may be absent. The photonic crystal patterned regions are kept free from any cover polymer. The cover polymer must be transparent at the wavelength of operation of the device. The cover polymer thus forms the top cladding for the sub-wavelength grating couplers, the MMIs, and the input and output ridge waveguides.

Figure 9:
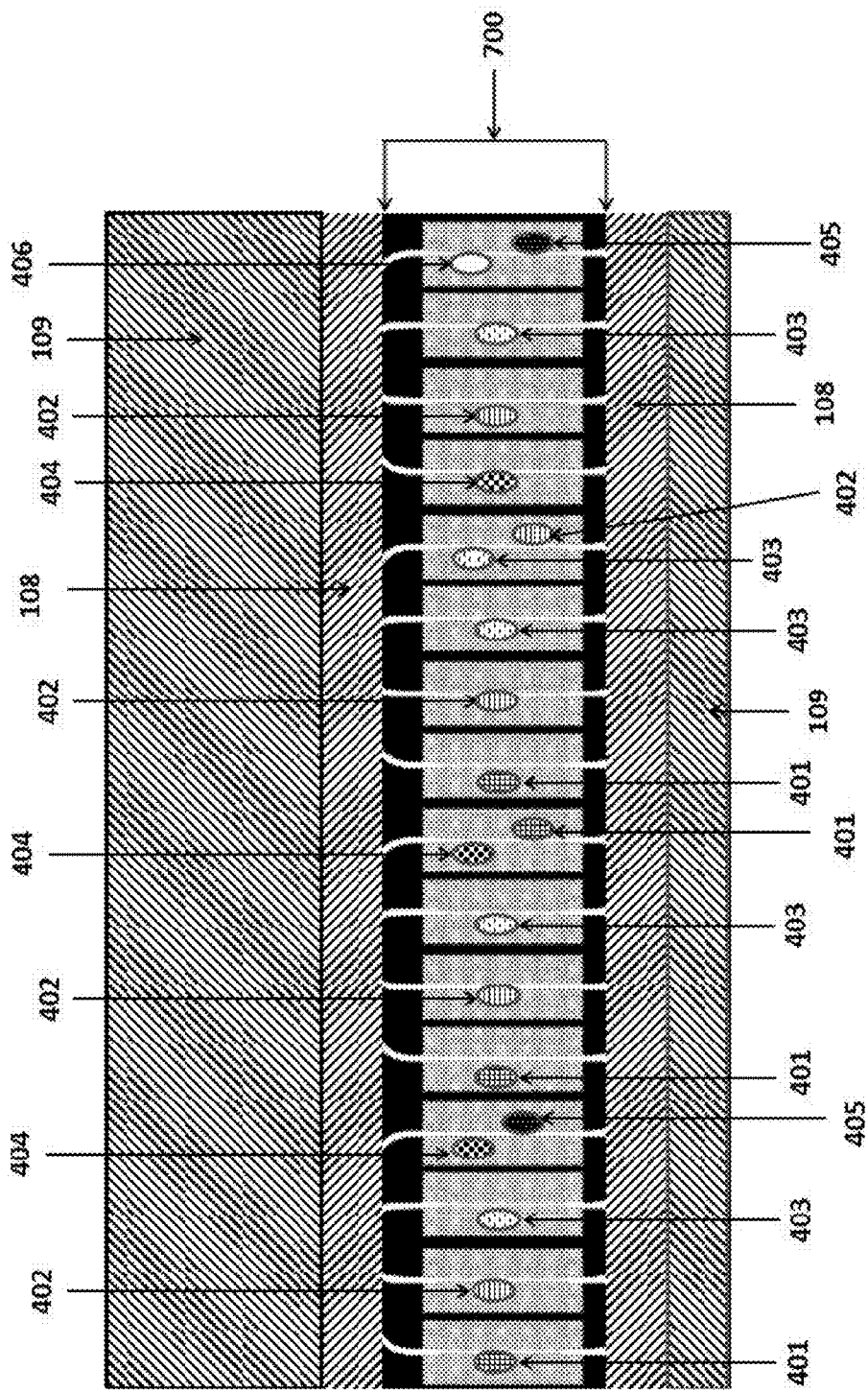
FIG. 9 is the top view of the device in FIG. 8 showing the disposition of one or more, same or different, polymer molecules or biomolecules on the one or more photonic crystal microcavities.

FIG. 9 is the top view of FIG. 8 which shows the individual polymer molecules or biomolecules 401, 402, 403, 404, 405, and 406 on top of the photonic crystal microcavities in each arm of the device. One or more photonic crystal microcavities may be coated with the same or different polymer molecule or biomolecule.

In one embodiment, the biomolecule can be proteins, nucleic acids, DNA, RNA, antigens, antibodies, small molecules, peptides, genes etc. Each biomolecule can be specific to a particular disease causing conjugate where the disease of interest can be cancer, malaria, leptospirosis, or any infectious disease to achieve specific detection. In another embodiment, the polymer molecule can be a hydrogel that swells in the presence of a specific analytical solution or ambient gas wherein the ambient gas includes, but is not limited to, greenhouse gases such as carbon dioxide, methane, nitrous oxide, or other gases such as oxygen, nitrogen, thereof. In yet another embodiment, the substance can be a polymer that changes its effective refractive index upon contact with a chemical substance or proportionately to changes in temperature, humidity, pressure, and/or ions in solution thereof.

Figure 10:
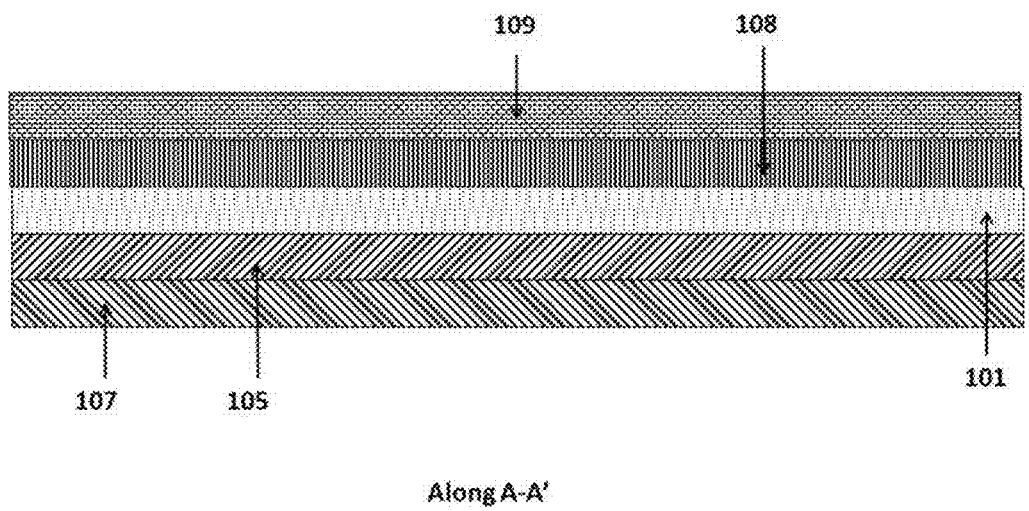
FIG. 10 is a cross-sectional view of the device in FIG. 2 along the plane A-A', and also including the top cover polymer layer and the rigid dielectric cover.

FIG. 10 is a cross-section of the device along the MMI 111 in the direction shown in FIG. 2 by the line A-A'. In FIG. 2, the top cover polymer and top rigid dielectric were not shown for clarity. In FIG. 8, the MMI 111 is located below the top cover polymer and the top rigid dielectric and is thus not visible. The cross-section thus shows the layer structure of the device at the location of the multimode interference power splitter, showing the substrate 107, the bottom cladding 105, the slab 101 into which the MMI 111 is defined, the top cover polymer 108, and the top rigid dielectric 109.

Figure 11:
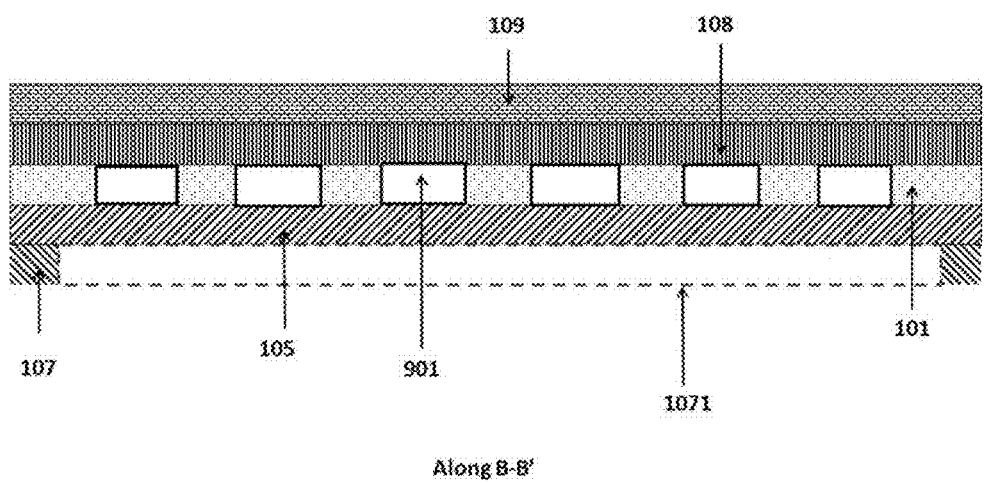
FIG. 11 is a cross-sectional view of the device in FIG. 5 along the plane B-B', and also including the top cover polymer layer and the rigid dielectric cover.

FIG. 11 is a cross-section of the device along the sub-wavelength grating coupler, at the input 111 in the direction shown in FIG. 5 by the line B-B'. In FIG. 5, the top cover polymer and top rigid dielectric were not shown for clarity. In FIG. 8, the sub-wavelength grating coupler 111 is located below the top cover polymer and the top rigid dielectric and is thus not visible. The cross-section thus shows the layer structure of the device at the location of the sub-wavelength grating coupler 200, showing the substrate 107, the bottom cladding 105, the slab 101 into which the sub-wavelength grating coupler 200 is defined, the top cover polymer 108 and the top rigid dielectric 109. Rectangular voids etched into the element 200 are indicated by 901. The voids 901 are partially or fully filled with the top cover polymer 108. A void 1071 is etched from the backside into the substrate 107. Light is incident into the sub-wavelength grating coupler from an external light source via the void 1071 in the substrate 107.

FIG. 12 is same as FIG. 1, except the photonic crystal patterned region comprises a photonic crystal slot waveguide with one or more rectangular voids or slots along the length of the photonic crystal waveguide, the input impedance taper in the photonic crystal waveguide, the output impedance taper in the photonic crystal waveguide and the input and output ridge waveguides from the photonic crystal pattern. Detailed description of FIG. 12 follows:

FIG. 12 presents a top view schematic drawing of a multiplexed photonic crystal slot waveguide device. It consists of a functional MMI 111 with one input arm 1110 which is a ridge waveguide and 4 representative output arms 1111, 1112, 1113, and 1114 which are four ridge waveguides. On each output arm 1111, 1112, 1113, and 1114, the second stage of a functional MMI is made. One skilled in the art will note that the number of output arms, shown as four in the figure can actually be any number n=1, 2, 3, 4, 5 . . . N. A representative second stage MMI on the arm 1112 is denoted as 122. The MMI 122 has four output arms 1221, 1222, 1223, and 1224 which are four ridge waveguides. Elements 1221, 1222, 1223, and 1224 have been shown in detail in FIG. 2 to avoid cluttering in FIG. 1. Only two (2) MMI stages are shown here, but one skilled in the art will note that the number of cascaded MMI stages can be cascaded m times where m=1, 2 . . . M.

FIG. 13 is an enlarged top view of the input section of the photonic crystal patterned regions 25, 26, 27, and 28 in FIG. 12. Each output arm 1221, 1222, 1223, and 1224 is a ridge waveguide that terminates in functional mode converter sections 1225, 1226, 1227, and 1228 respectively that transform the optical mode propagating down a conventional ridge waveguide into a slot waveguide or slotted ridge waveguide as defined by 351, 361, 371, and 381 respectively. The slot waveguides or slotted ridge waveguides 351, 361, 371, and 381 are defined by one or more rectangular slots or voids 35, 36, 37, and 38 respectively etched through the ridge waveguide. The core of the photonic crystal patterned region 26 comprises a functional photonic crystal waveguide 12222, an input impedance taper 12221 between the input slot waveguide 361 and the photonic crystal waveguide 12222, and an output impedance taper 12223 between the output slot waveguide 461 and the photonic crystal waveguide 12222. The one or more rectangular slots or voids 36 for instance extend along the entire length of the functional photonic crystal waveguide 12222, the input impedance taper 12221, and the output impedance taper 12223. An output slot mode converter 12261 converts the propagating optical mode in the slot waveguide 461 to a ridge waveguide optical mode in the output ridge waveguide 2060. A similar description applies to the output slot mode converters 12251, 12271 and 12281.

The photonic crystal patterned regions 25, 26, 27, and 28 include a number of column members 102 etched through or partially into the semiconductor slab 101. Within each photonic crystal patterned region, the waveguide core 141 is defined as the space between the centers of two column members adjacent to the region where the columns are filled with the material of the slab. In one preferred embodiment, the column members 102 are arranged to form a periodic lattice with a lattice constant α. In some embodiments, the width of waveguide core 141 can range from 0.5 times sqrt(3) times the lattice constant or period α to 50 times sqrt(3) times the lattice constant or period α.

Light is coupled into the input arm 1110 of the MMI 111 via a sub-wavelength grating coupler 200. The output light from each output ridge waveguide, in one instance, the output ridge waveguide 2050 is coupled out of the plane of the slab 101 by an output sub-wavelength grating coupler 205. Sub-wavelength grating couplers 201, 202, 203 . . . 216 couple light out from the output ridge waveguides 2010, 2020, 2030 . . . 2160 respectively out of the plane of the slab 101.

FIG. 14 is a schematic cross-section of the photonic crystal patterned region in FIG. 13 taken along the plane D-D'. FIG. 14 shows the substrate 107, the bottom cladding 105 disposed on the substrate, the semiconductor slab 101 disposed on the bottom cladding with columnar members 102 etched through the slab. The rectangular slot or void etched in the middle of the photonic crystal waveguide is indicated by 36. A hydrophobic polymer 106 forms the top cladding. One skilled in the art will note that columnar members 102 and rectangular slot 36 can extend through 101 as well as through the bottom cladding 105 to reach the substrate 107. The material of the top cladding 106 can fill the columnar members 102 and the slot 36 either fully or partially during device operation. Although the structure within the slab 101 is substantially uniform in the vertical direction in this embodiment, one skilled in the art will understand that vertically non-uniform structure, such as the columnar members 102 whose radii are varying along the vertical direction, may be used as well.

FIG. 15 is the top view of the packaged device showing the layout of the chip in FIG. 1 or FIG. 12 in the package or shell 600. The package shell comprises a top portion, a bottom portion, and a side wall portion which together surround an interior volume. The side wall portion of the package shell may comprise four side walls. Alternatively, the side wall portion may comprise one or more side walls. In the case of a single side wall, the resulting shell is cylindrical. Square grooves 601, 602, 603, and 604 are made at the four corners of the package. The package 600 may be ceramic, plastic, or any material which provides toughness and environmental protection to the internal semiconductor chip. The opening in the package 701 on the top side is aligned with the microfluidic channel opening 700 in the semiconductor chip.

FIG. 16 is the bottom view of the package. Opening 1071 is made in the package aligned with the position of the sub-wavelength grating coupler 200 on the semiconductor chip. The size of the opening 1071 is larger than the size of the sub-wavelength grating coupler 200. Opening 1072 is made in the package aligned with the positions of all the output sub-wavelength grating couplers 201, 202, 203 . . . 216. The size of the opening 1072 is larger than the area covered by all the sub-wavelength grating couplers 201, 202, 203 . . . 216.

FIG. 17 is a cross-sectional view taken along the plane E-E' in FIG. 16 through the input sub-wavelength grating coupler 200. FIG. 17 shows the layout of the semiconductor chip within the package 600. A hole or void is etched into the substrate 107 of the semiconductor chip. The opening 1071 in the bottom of the package aligned with the input sub-wavelength grating coupler 200 is shown. The sub-wavelength grating coupler rests on the bottom cladding 105. The rectangular voids 901 of the sub-wavelength grating coupler in the slab 101 are shown. The top cover polymer 108 and the rigid dielectric cover 109 are also shown. The top cap of the package 600 is finally shown. In some embodiments, the rigid dielectric cover 109 may be absent and the top cap of the package 600 is located on top of the cover polymer 108.

On the input sub-wavelength grating coupler 200, light is incident from an external optical source into the chip via the sub-wavelength grating couplers in the direction as indicated by the broad bold arrow in FIG. 17. At the output sub-wavelength grating couplers 201, 202, 203 . . . 216, light exits from the sub-wavelength grating couplers in the direction as indicated by the bold dashed arrow in FIG. 19. Although the arrows have been drawn to achieve normal incidence into and normal emission from sub-wavelength grating couplers, one skilled in the art will note that the sub-wavelength grating couplers can be designed to achieve maximum coupling efficiency into and out of the semiconductor chip by considering an angle of incidence φ from the out-of-plane normal to the sub-wavelength grating where φ can vary continuously from zero to forty degrees and from zero to negative forty degrees.

FIG. 18 is the top view of a second embodiment of the packaged optical chip showing the layout of the chip in FIG. 1 or FIG. 12 in the package 600. Square grooves 601, 602, 603, and 604 are made at the four corners of the package. The package 600 may be ceramic, plastic, or any material which provides toughness and environmental protection to the internal semiconductor chip. The opening in the package 701 on the top side is aligned with the microfluidic channel opening 700 in the semiconductor chip. Openings are made in the package 600 as bordered by the segments 1071 and 1072. The element 109 is also voided in the region bordered by 1071 and 1072 so that the element 108 is exposed. In essence, light is then coupled into the semiconductor chip from the top of the chip from external optical sources and through the top cover polymer cover 108. Similarly, light is coupled out of the semiconductor chip from the top of the chip to external optical detectors and through the top cover polymer cover 108.

FIG. 19 is a cross-sectional view taken along the plane F-F' in FIG. 18 through the input sub-wavelength grating coupler 200. FIG. 19 shows the layout of the semiconductor chip within the package 600. A hole or void is made in the package 600 and in the element 109 in the regions bordered by 1071 and 1072. The sub-wavelength grating coupler rests on the bottom cladding 105. The rectangular voids 901 of the sub-wavelength grating coupler in the slab 101 are shown. The top cover polymer 108 and the rigid dielectric cover 109 are also shown. In some embodiments, the rigid dielectric cover 109 may be absent and the top cap of the package 600 is located on top of the cover polymer 108.

FIG. 20 is the top view of a third embodiment of the packaged optical chip showing the layout of the chip in FIG. 1 or FIG. 12 in the package 600. Square grooves 601, 602, 603, and 604 are made at the four corners of the package. The package 600 may be ceramic, plastic, or any material which provides toughness and environmental protection to the internal semiconductor chip. The opening in the package 701 on the top side is aligned with the microfluidic channel opening 700 in the semiconductor chip. Openings are made in the package 600 as bordered by the segments 1071 and 1072. The elements 108 and 109 are also voided in the region bordered by 1071 and 1072 so that the input sub-wavelength grating coupler 200 and the output sub-wavelength grating couplers 201, 202, 203 . . . 216 are exposed. In essence, light is then coupled into the semiconductor chip from the top of the chip from external optical sources and directly into the input sub-wavelength grating coupler 200. Similarly, light is coupled out of the semiconductor chip from the top of the chip to external optical detectors and directly from the output sub-wavelength grating couplers 201, 202, 203 . . . 216.

FIG. 21 is a cross-sectional view taken along the plane G-G' in FIG. 20 through the input sub-wavelength grating coupler 200. FIG. 21 shows the layout of the semiconductor chip within the package 600. A hole or void is made in the package 600 and in the elements 108 and 109 in the regions bordered by 1071 and 1072. The opening 1071 in the top of the package aligned with the input sub-wavelength grating coupler 200 is shown. The sub-wavelength grating coupler rests on the bottom cladding 105. The rectangular voids 901 of the sub-wavelength grating coupler in the slab 101 are shown. The top cover polymer 108 and the rigid dielectric cover 109 are also shown. In some embodiments, the rigid dielectric cover 109 may be absent and the top cap of the package 600 is located on top of the cover polymer 108.

FIG. 22 is a bottom view of the packages described by FIGS. 18 and 19. FIG. 22 is also the bottom view of the package described by FIGS. 20 and 21. Square grooves 601, 602, 603, and 604 made at the four corners of the package can be seen.

Figure 23A:
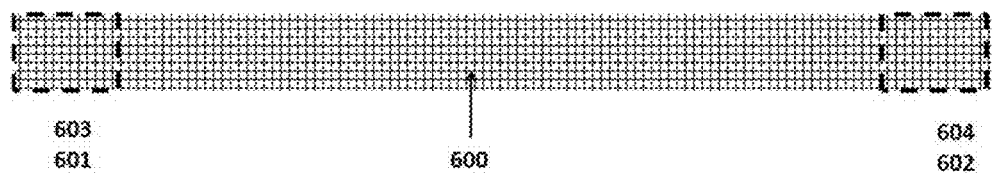
Figure 23B:
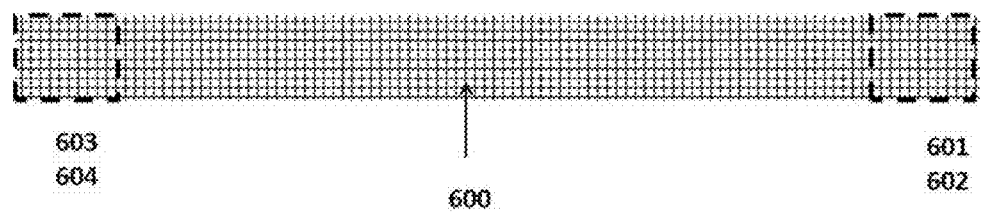
Figure 24A:
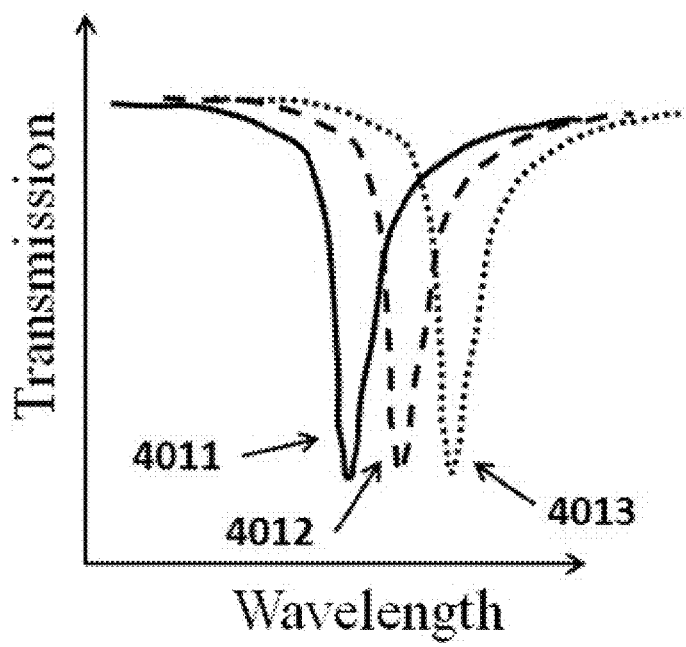
Figure 24B:
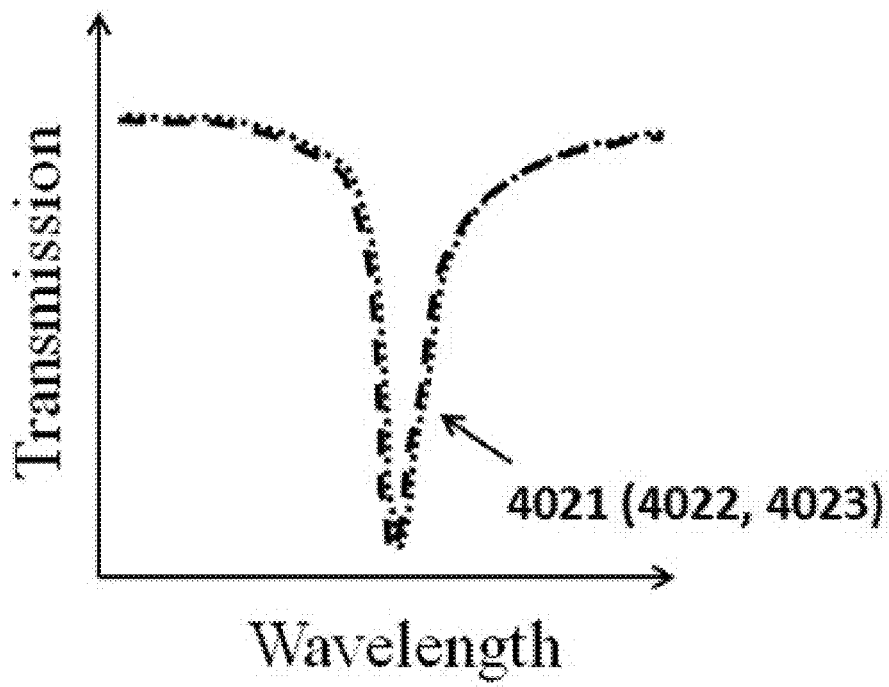
Figure 24C:
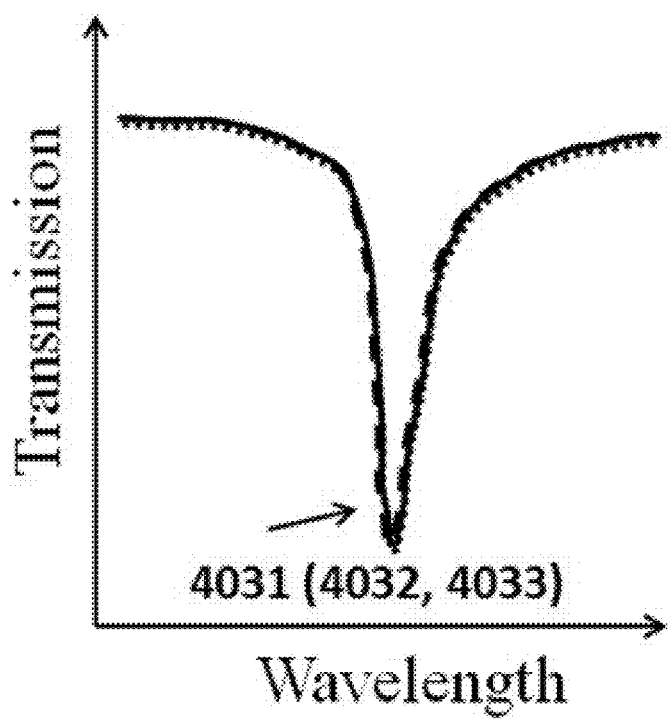
Figure 24D:
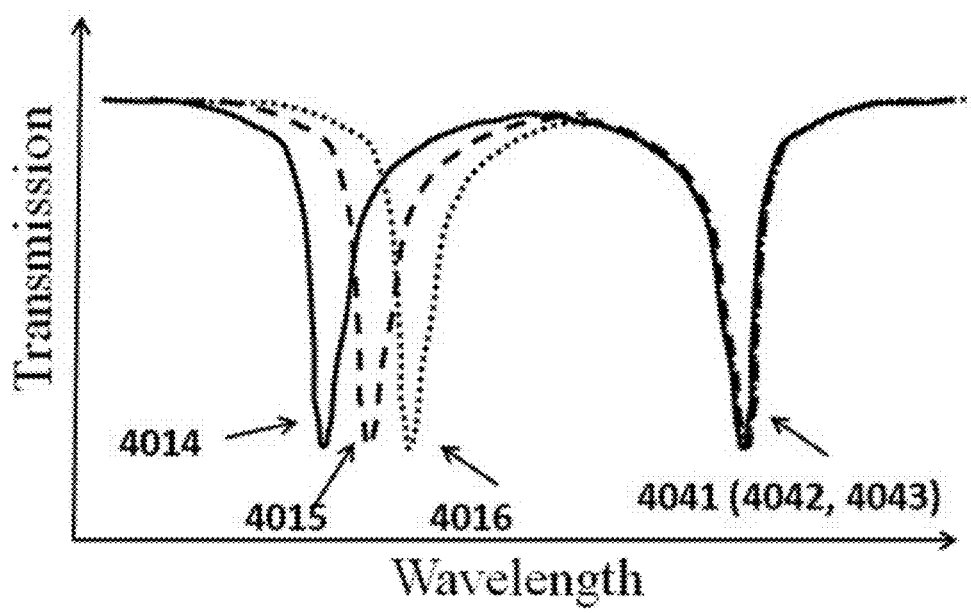

FIG. 23A is a view of the package described in FIGS. 15-22 observing from the end J or J' in FIG. 22. FIG. 23B is a view of the package described in FIGS. 15-22 observing from the end K or K' in FIG. 22. The positions of the grooves 601, 602, 603, and 604 are also indicated.

FIG. 24A, FIG. 24B, FIG. 24C, and FIG. 24D show the transmission output spectra from the output sub-wavelength grating couplers 205, 206, 207, and 208 respectively. From FIG. 8, we note that the ridge waveguides that output to the output sub-wavelength grating couplers 205, 206, 207, and 208 are respectively numbered as 2050, 2060, 2070, and 2080. We also note from FIG. 8 that the ridge waveguides output from the photonic crystal patterned regions 21, 22, 23, and 24 respectively. From FIG. 9 we note that the photonic crystal microcavity in the patterned region 21 is coated with a biomolecule 401, the photonic crystal microcavity in the patterned region 22 is coated with a biomolecule 402, the photonic crystal microcavity in the patterned region 23 is coated with a biomolecule 403, and the two photonic crystal microcavities in the patterned region 24 are coated with biomolecules 401, same as in the patterned region 21, and a different biomolecule 404.

FIG. 24 illustrates a typical transmission spectrum from the 4 output arms of a 1×4 MMI with a photonic crystal waveguide coupled microcavity in each arm. The microcavity sensors in output arms #1, #2, and #3 are coated with unique target receptor biomolecules T1, T2, and T3. Microcavity sensors in arm #4 are coated with target receptor biomolecules T1 and T4. When a sample solution containing only the probe biomolecule P1 which binds specifically to biomolecule T1 and does not bind to any of biomolecules T2 or T3, only the resonance wavelength in arm #1 and the resonance in one of the microcavities in arm #4 coated with target receptor biomolecule T1 shifts. Resonances in arms #2 and #3 do not shift. The resonance wavelength of the second microcavity in arm #4 does not change. When a sample solution containing the secondary antibody S2 which binds specifically to probe biomolecule P1 and does not bind to any of T2, T3, or T4 is now introduced, a secondary resonance wavelength shift in arm #1 and the first microcavity in arm #4 occurs. Resonances in arms #2 and #3 do not shift. Resonance wavelength of the second microcavity in arm #4 does not change as well. Binding specificity is thus confirmed from the multiplexed sandwich detection of the specific probe P1. Control antibodies T2 and T3 also confirm specificity by showing no binding response to the probe biomolecule P1. In FIG. 24A, FIG. 24B, FIG. 24C, and FIG. 24D, the solid black curves represent the baseline transmission spectrum obtained from the output sub-wavelength grating couplers 205, 206, 207, and 208 respectively, when the photonic crystal microcavities in the corresponding photonic crystal patterned regions 21, 22, 23, and 24 respectively are coated with biomolecules 401, 402, 403, and (401 and 404) respectively and the device is immersed in the analyte 106 that fills the area in the microfluidic channel 700 as described before in FIG. 9. The resonance wavelengths from each of 205, 206, 207, and 208 are denoted by 4011, 4021, 4031, and (4014 and 4041) respectively. When an analyte 106 containing the probe biomolecule P1 which is the specific conjugate of the target biomolecule 401 is introduced, the new positions of the resonance wavelengths in each of FIG. 24A, FIG. 24B, FIG. 24C, and FIG. 24D are denoted by the black dashed curves. The resonance wavelength 4011 shifts to 4012 and the resonance wavelength 4014 shifts to 4015. Other resonance wavelength 4021, 4031, and 4041 do not shift at all and thus 4022, 4032, and 4042 are the same as 4021, 4031, and 4041. To confirm that the biomolecule P1 that bound to 401 is a specific conjugate of 401, an analyte 106 containing the secondary antibody S2 is introduced in the device microfluidic channel, and the corresponding new positions of the resonance wavelengths in each of FIG. 24A, FIG. 24B, FIG. 24C, and FIG. 24D are denoted by the black dotted curves. The resonance wavelengths 4012 and 4015 further shift to 4013 and 4016, respectively, while the resonance wavelengths 4022, 4032, and 4042 remain at the same position as denoted by 4023, 4033, and 4043. The lack of any resonance wavelength shift from the photonic crystal microcavities coated with 402, 403 and 404 and the multiplexed observation of resonance wavelength shift from the photonic crystal microcavities coated with 401 in the same measurement, together with the secondary resonance wavelength shift observed upon the introduction of the secondary antibody S2, validate the method by which binding specificity is achieved by multiplexed experiments in the same measurement. We emphasize "same measurement" because light is incident into the input sub-wavelength grating coupler 200 and is collected from all output sub-wavelength grating couplers 201, 202, 203 . . . 216 at the same time.

While the measurement has been described with respect to biomolecules, one skilled in the art will note that the discussion in FIG. 24 is applicable to polymer molecules that respond to specific chemical signatures, or ambient conditions such as ion concentration in solution, gas concentration in ambient, temperature, pressure, or humidity.

In FIG. 25, we describe one embodiment of the output waveguide configuration to output light from all the output waveguides 2010, 2020, 2030 . . . 2160 using a single multimode interference power combiner 309. The output from the multimode interference power combiner inputs light into a single output sub-wavelength grating coupler 300. One skilled in the art will note that the same output device structure described by FIG. 25 holds for the photonic crystal slot waveguide structure described by FIG. 12.

In FIG. 26, we describe a second embodiment of the output waveguide configuration to output light from all the output waveguides 2010, 2020, 2030 . . . 2160 using cascaded stages of multimode interference power combiners 321, 322, 323, and 324 that finally output to a single multimode interference power combiner 325. The output from the multimode interference power combiner 325 inputs light into a single output sub-wavelength grating coupler 300. One skilled in the art will note that the same output device structure described by FIG. 26 holds for the photonic crystal slot waveguide structure described by FIG. 12.

In FIG. 27, we describe a third embodiment of the output waveguide configuration to output light from all the output waveguides 2010, 2020, 2030 ... 2160 using cascaded stages of Y-junction ridge waveguide power combiners 821, 822, 823 ... 835 that finally output to a single output sub-wavelength grating coupler 300. A Y-junction ridge waveguide may also be described as two-to-one ridge waveguide junctions. One skilled in the art will note that the same output device structure described by FIG. 27 holds for the photonic crystal slot waveguide structure described by FIG. 12. One skilled in the art will also note that cascaded stages of Y-junction ridge waveguide power combiners may also be used at the input end as Y-junction one-to-two ridge waveguide power splitters replacing all the multimode interference power splitters at the input end in order to couple light from the input sub-wavelength grating coupler 200 to each of the sixteen photonic crystal patterned regions in FIG. 1 and into each of the sixteen mode converters just preceding the input of the sixteen photonic crystal patterned regions in FIG. 12. The mode converter in FIG. 12 preceding each photonic crystal patterned region that converts the input optical mode from ridge waveguide mode to slotted ridge waveguide mode has been shown in detail in FIG. 13.

FIG. 28A, FIG. 28B, FIG. 28C, and FIG. 28D show characteristic transmission spectra observed on the output sub-wavelength grating couplers 205, 206, 207, and 208 separately when the photonic crystal patterns 21, 22, 23, and 24 on the corresponding arms have the same lattice constant.

FIG. 28E confirms that in the embodiments described by FIG. 3, when separate photonic crystal patterns 21, 22, 23, and 24 have the same lattice constant, the transmission spectra from all the sub-wavelength grating couplers are measured separately by separate external optical fibers or separate external photodetectors. Thus if all the outputs of FIG. 28A, FIG. 28B, FIG. 28C, and FIG. 28D were combined into a single output, it would not be possible to distinguish the separate resonances of the photonic crystal microcavities from the separate photonic crystal patterns 21, 22, 23, and 24.

FIG. 29A, FIG. 29B, FIG. 29C, and FIG. 29D show characteristic transmission spectra observed on the output sub-wavelength grating couplers 205, 206, 207, and 208 separately when the photonic crystal patterns 21, 22, 23, and 24 on the corresponding arms have different lattice constants. In this way, instead of separate output sub-wavelength grating couplers 201, 202, 203 ... 216, as shown in FIG. 3, we can have a single output sub-wavelength grating coupler 300, as described in FIGS. 25, 26, and 27, so that a combined transmission spectrum as shown in FIG. 29E is obtained at the single output sub-wavelength grating coupler 300. In contrast to FIG. 28E, it is possible in FIG. 29E to distinguish the separate resonances of the photonic crystal microcavities from the separate photonic crystal patterns 21, 22, 23, and 24 from the combined output of the single output sub-wavelength grating coupler 300.

In FIG. 30, the external optical fiber 609 at the input sub-wavelength grating coupler is glued to the package 600 via an ultra-violet cured polymer 610 such as epoxy. Although FIG. 30 has been shown for the input sub-wavelength grating coupler, one skilled in the art will note that the configuration described by FIG. 30 is the same for all output sub-wavelength grating couplers as described by FIGS. 1 and 12, using a separate fiber 609 for each output sub-wavelength coupler 201, 202, 203 ... 216 or a single fiber 609 for all the output sub-wavelength grating couplers 201, 202, 203 ... 216. One skilled in the art will also note that the same configuration as FIG. 30 also holds for the cross-section across the single output sub-wavelength grating couplers 300 shown in FIGS. 25, 26 and 27. The external optical fiber is aligned at an angle ϕ where ϕ may vary continuously from zero degrees to forty (40) degrees as determined by the designed angle for maximum optical coupling efficiency with the sub-wavelength grating coupler at both the input and output.

In FIG. 31, the external optical fiber 609 is polished at an angle ϕ as determined by the angle ϕ for maximum coupling efficiency in FIG. 30 for incident light into the input sub-wavelength grating coupler or exiting light from the output sub-wavelength grating couplers to the external optical fiber at the output. The dashed arrow shows the direction of light coupling at the input. One skilled in the art will note that the direction of light coupling at the output essentially reverses the direction of the dashed arrow. In one embodiment, a reflecting material such as gold is deposited on the polished facet 611 to enhance the optical coupling efficiency. While FIG. 31 has been drawn for the case of coupling light into and out of the input and output sub-wavelength grating couplers respectively from the bottom of the device, one skilled in the art will note that the method of optical coupling with optical fibers with polished facets and gold deposited on the polished facets for enhanced coupling efficiency is also applicable for coupling in and out of the device from the top of the device as illustrated in FIG. 19 and FIG. 21.

In FIG. 32, the output waveguides 2010, 2020 ... 2160 are bent by 180 degrees so that the output sub-wavelength grating couplers 201, 202, 203 ... 216 are on the same side of the photonic crystal pattern as the input sub-wavelength grating coupler 200. In this configuration, a single optical fiber bundle consists of individual optical fibers in which one optical fiber couples light into the input sub-wavelength grating coupler 200 and the other optical fibers receive light from the output sub-wavelength grating couplers 201, 202 ... 216. In this configuration of FIG. 32, if the center-to-center spacing between the sub-wavelength grating couplers 201, 202 ... 208, 200, 209, 210 ... 216 in order is known and the external optical fiber bundle has the same center-to-center spacing between individual cores of the external optical fibers as the center-to-center spacing between the sub-wavelength grating couplers 201, 202 ... 208, 200, 209, 210 ... 216 in order, then one needs to perform only one optical alignment, for instance of 201 with one external optical fiber in the bundle to ensure that all optical fibers in the bundle are aligned to the respective sub-wavelength grating couplers on the chip. In contrast, in FIG. 1 and FIG. 12, one would need two separate optical fiber bundles, one bundle for the input sub-wavelength grating coupler or couplers, and one bundle for the output sub-wavelength grating couplers. Thus, during chip-packaging with external optical fibers, one will need to perform two optical alignments, one with the set of input sub-wavelength grating coupler or couplers only, and the other with the set of output sub-wavelength grating couplers. Chip-packaging difficulty is thus reduced in FIG. 32. One skilled in the art will note, that the output waveguides 3000 in each of FIGS. 25, 26, and 27 can also be bent around by 180 degrees so that the output sub-wavelength grating coupler 300 in each figure is adjacent to the input sub-wavelength grating coupler 200 so that a single optical fiber bundle with two optical fibers in the bundle can be used to couple light into the input sub-wavelength grating coupler 200 from one fiber and couple light out from the output sub-wavelength grating coupler 300 from the second fiber in the bundle.

FIG. 33A, FIG. 33B, FIG. 33C, and FIG. 33D show characteristic transmission spectra at the output ridge waveguides 2050, 2060, 2070, and 2080 separately in FIG. 13 when the photonic crystal patterns 25, 26, 27, and 28 on the corresponding arms have different lattice constants. The photonic crystal slot waveguides in each patterned region 25, 26, 27, and 28 thus have different transmission spectra with different transmission band edges. The individual transmission spectra of the output ridge waveguides 2050, 2060, 2070, and 2080 in FIG. 13 can also be observed at the corresponding output sub-wavelength grating couplers 205, 206, 207, and 208 in FIG. 12. The slow light effect is maximum near the transmission band edge for each photonic crystal slot waveguide. We assume that each of the indicated wavelengths $\lambda y_5$, $\lambda y_6$, and $\lambda y_7$, between the range of $\lambda_1$ and $\lambda_2$, in FIG. 33 denote wavelengths at which three separate analytes (whose absorption or absorbance is denoted by the respective spectra A5, A6, and A7 in FIG. 33E) have peak absorption. We also consider another wavelength $\lambda y_8$ in FIG. 33E at which all the above three analytes have zero absorbance. The lattice constant of the photonic crystal patterns and the diameter of the columnar members 102 and the width of the slot 36 as shown in FIG. 14 in each of the photonic crystal patterned regions 25, 26, 27, and 28 is chosen so that the transmission band edge is near the individual absorption peaks $\lambda y_5$, $\lambda y_6$, and $\lambda y_7$ for 25, 26 and 27, and near $\lambda y_8$ for 28. Thus there is maximum slow light enhanced absorbance for each of the analytes whose absorption or absorbance is denoted by the respective spectra A5, A6, and A7 at their individual peak absorbances at $\lambda y_5$, $\lambda y_6$, and $\lambda y_7$. At $\lambda y_8$ on the photonic crystal patterned region 28, where none of the three chosen analytes absorb, the magnitude of the slow light effect is kept similar to the other photonic crystal patterned regions 25, 26, and 27. The absorption spectra of A5, A6, and A7 do not overlap with each other at their respective peak absorbances at $\lambda y_5$, $\lambda y_6$, and $\lambda y_7$, as indicated in FIG. 33E. Hence, there is no interference to the absorbance measurements of one analyte in one photonic crystal patterned region 25 for instance at $\lambda y_5$, by the absorbance measurements of the second analyte in the second photonic crystal patterned region 26 for instance at $\lambda y_6$. The magnitude of absorbance for each of the three analytes whose absorbance spectra are denoted by A5, A6, and A7 is determined by performing three sets of transmission measurements respectively at ($\lambda y_5$ and $\lambda y_8$), at ($\lambda y_6$ and $\lambda y_8$), and at ($\lambda y_7$ and $\lambda y_8$). Since there should be no change in transmission intensity at $\lambda y_8$ due to zero absorbance of the three analytes, hence a zero change in transmission intensity measured at $\lambda y_8$ serves as a reference that ensures that there has been no change in the intensity of the electromagnetic radiation generated by the incident broadband source. If there is a change in transmission intensity at $\lambda y_8$, then the change in transmission intensity at $\lambda y_5$ for the analyte with absorbance spectrum denoted by A5 is adjusted by the magnitude of the change in transmission intensity at $\lambda y_8$. A similar measurement method is applied at $\lambda y_6$ and $\lambda y_7$ for analytes with absorbance denoted by A6 and A7 respectively. The photonic crystal slot waveguide within the photonic crystal pattern 28 thus serves as a reference photonic crystal slot waveguide. Furthermore, if the output waveguides 2050, 2060, 2070, and 2080 are combined in the configurations described in FIGS. 25, 26, and 27, the absorbance of each analyte can be measured from one single output as described by FIG. 33F, by measuring the transmission intensity changes at $\lambda y_5$, $\lambda y_6$, $\lambda y_7$, and $\lambda y_8$ respectively.

In one embodiment, the slab 101 is formed from a material of high refractive index including, but not limited to, silicon, germanium, carbon, gallium nitride, gallium arsenide, gallium phosphide, indium nitride, indium phosphide, indium arsenide, zinc oxide, zinc sulfide, silicon oxide, silicon nitride, alloys thereof, metals, and organic polymer composites. Single crystalline, polycrystalline, amorphous, and other forms of silicon may be used as appropriate. Organic materials with embedded inorganic particles, particularly metal particles, may be used to advantage. In one embodiment, the top cladding 106 and bottom cladding 105 are formed from a material whose refractive index is lower than that of the slab material. Suitable top cladding and bottom cladding materials include, but not limited to, air, silicon oxide, silicon nitride, alumina, organic polymers and alloys thereof. The substrate 107 materials include, but not limited to, silicon, gallium arsenide, indium phosphide, gallium nitride, sapphire, glass, polymer and alloys thereof. In one embodiment, the columnar members 102 are formed from a material whose refractive index is substantial different from that of the slab 101. Suitable materials for the columnar members 102 include, but not limited to, air, silicon oxide, silicon nitride, alumina, organic polymers, or alloys thereof. In one preferred embodiment, the slab 101 is formed from silicon, the columnar members 102 are formed from air, the top cladding 106 is the analyte medium, and the bottom cladding 105 is formed from silicon oxide, while the substrate 107 is silicon. In another embodiment, the slab 101 is formed from germanium. The bottom cladding 105 is a low dielectric constant material with transparency in the near-, mid-, and far-infrared such as but not limited to silicon dioxide or silicon nitride, barium fluoride, yttrium fluoride, ytterbium fluoride, cerium fluoride, or dysprosium fluoride. The substrate 107 is but not limited to silicon, gallium arsenide, indium phosphide, sapphire, barium fluoride. The material for the substrate 107, bottom cladding 105, and the slab 101 are chosen so that they are optically transparent in the wavelength of operation, and the dielectric constant of the bottom cladding 107 is lower than the dielectric constant of the slab 101.

Although the word "biomolecule" is used in the preceding discussions, one skilled in the art will understand that it refers to a general form of biomolecule that includes, but not limited to, proteins, deoxyribonucleic acid (DNA), ribonucleic acid (RNA), genes, antigens, antibodies, small molecules, nucleic acids, bacteria, viruses and any arrayed combination thereof for the specific diagnosis of diseases. "Molecule" can denote any polymer or hydrogel that responds to changes in the ambient medium of the device. Any combination of "molecules" and "biomolecules" can be arrayed on the device to get precise knowledge of process conditions, system conditions, analyte identification and/or binding events for disease identification.

Although the word "analyte" is used in the preceding discussions, one skilled in the art will understand that it refers to a general form of analyte that includes solids, liquids, and gases.

Although the word "light" or "lightwave" is used to denote signals in the preceding discussions, one skilled in the art will understand that it refers to a general form of electromagnetic radiation that includes, and is not limited to, visible light, infrared light, ultra-violet light, radios waves, and microwaves.

In summary, the present invention provides a packaging layout for multiplexing several optical waveguides in the photonic crystal platform using sub-wavelength grating couplers for efficient optical coupling in a compact package.

While the invention has been described in connection with a number of preferred embodiments, it is not intended to limit the scope of the invention to the particular form set forth, but on the contrary, it is intended to cover such alternatives, modifications, and equivalents as may be included within the design concept of the invention as defined by the appended claims.

The invention claimed is:

1. A packaged chip for the integration of arrays of photonic crystal microcavity coupled waveguides with external optical sources and external optical detectors comprising:

i) a package shell comprising a top portion, a bottom portion, and a side wall portion which together surround an interior volume;
ii) a substrate disposed on the interior side of the bottom portion of the package shell and bounded by the interior side of the side wall portion of the package shell;
iii) a bottom cladding disposed on the substrate and bounded by the interior side of the side wall portion of the package shell;
iv) a slab disposed on the bottom cladding and bounded by the interior side of the side wall portion of the package shell, wherein the refractive index of the bottom cladding is lower than the refractive index of the slab;
v) a cover polymer disposed on the slab, wherein the cover polymer is capped by the interior side of the top portion of the package shell and bounded by the interior side of the side wall portion of the package shell;
vi) an input sub-wavelength grating coupler comprising a plurality of void columnar members with rectangular cross-section etched through the slab, wherein the plurality of void columnar members have a periodicity $\beta$ in one direction along the slab and a periodicity $\gamma$ in the direction orthogonal to $\beta$ along the slab;
vii) a first multimode interference power splitter comprising:
 a) a first input end;
 b) a first output end;
 c) a first rectangular mesa defined in the slab;
 d) wherein the first rectangular mesa is coupled by a first ridge waveguide to the input sub-wavelength grating coupler at the first input end of the first multimode interference power splitter; and
 e) wherein the first rectangular mesa is coupled to one or more ridge waveguides at the first output end of the first multimode interference power splitter;
viii) a cascade of one or more multimode interference power splitters, wherein each of the one or more multimode interference power splitters comprises:
 a) an input end;
 b) an output end;
 c) a rectangular mesa defined in the slab;
 d) wherein the rectangular mesa at the input end of each of the one or more multimode interference power splitters is coupled to one of the one or more ridge waveguides at the first output end of the first multimode interference power splitter or to the output end of one or more multimode interference powers splitters; and
 e) wherein the rectangular mesa at the output end of each of the one or more multimode interference power splitters is coupled to one or more ridge waveguides;
ix) one or more photonic crystal microcavity coupled waveguides comprising:
 a) an input side, wherein the input side is coupled to the output end of one of the one or more multimode interference power splitters;
 b) an output side;
 c) a plurality of void columnar members with circular cross-section etched through the slab;
 d) a core in the slab formed by a row of void columnar members, wherein the row of void columnar members is filled with the material of the slab and wherein the plurality of void columnar members surround the core in the slab and form a periodic triangular or square lattice comprising one or more lattice constants, $\alpha$s;
 e) one or more optical microcavities formed by a group of columnar members, wherein the group of columnar members is filled with the material of the slab and wherein the one or more optical microcavities are separated from each other and the core in the slab by one or more lattice constants;
x) wherein the one or more photonic crystal microcavity coupled waveguides support one or more guided modes of a broadband source;
xi) wherein each of the one or more optical microcavities support one or more resonance modes;
xii) wherein the one or more optical microcavities with one or more target binding molecules coated on the one or more optical microcavities support one or more resonance modes comprising one or more resonant frequencies resulting in minima in a transmission spectrum of the one or more guided modes of the broadband source at the corresponding resonant frequencies of the one or more optical microcavities;
xiii) wherein one or more analytes selectively bind to the one or more target binding molecules resulting in shifting the resonance frequencies of the one or more optical microcavities and hence the minima in the transmission spectrum of the one or more guided modes of the broadband source in each photonic crystal waveguide;
xiv) wherein, the cover polymer disposed on the slab has void openings above the area of the one or more photonic crystal microcavity coupled waveguides to form one or more microfluidic channels;
xv) wherein, the package shell has void openings aligned with the one or more microfluidic channels; and
xvi) wherein, the package shell has void openings aligned with the input sub-wavelength grating coupler.

2. The packaged chip of claim 1, further comprising:
i) one or more output sub-wavelength grating couplers coupled to the output side of the one or more photonic crystal microcavity coupled waveguides;
ii) wherein the substrate has void openings aligned with the one or more output sub-wavelength grating couplers or the cover polymer disposed on the slab has void openings aligned with the one or more output sub-wavelength grating couplers; and
iii) wherein the package shell has void openings aligned with the one or more output sub-wavelength grating couplers.

3. The packaged chip of claim 2, wherein the one or more resonance modes are unique along each of the one or more photonic crystal microcavity coupled waveguides.

4. The packaged chip of claim 1, further comprising one or more multimode interference power combiners comprising:
i) an input end;
ii) an output end;
iii) a rectangular mesa defined in the slab;
iv) wherein the rectangular mesa at the input end of one of the one or more multimode interference power combiners is coupled by a ridge waveguide to the output side of the one or more photonic crystal microcavity coupled waveguides or the output end of one of the one or more multimode interference power combiners; and
v) wherein the rectangular mesa at the output end of the one or more multimode interference power combiners is coupled to one or more output sub-wavelength grating couplers; and
vi) wherein the package shell has void openings aligned with the one or more output sub-wavelength grating couplers.

5. The packaged chip of claim 4, wherein the one or more resonance modes are unique along each of the one or more photonic crystal microcavity coupled waveguides.

6. The packaged chip of claim 4, wherein the substrate has void openings aligned with the one or more output sub-wavelength grating couplers or the cover polymer disposed on the slab has void openings aligned with the one or more output sub-wavelength grating couplers.

7. The packaged chip of claim 1, further comprising the output side of the one or more photonic crystal microcavity coupled waveguides coupled to one or more two-to-one ridge waveguide junctions; one of the one or more two-to-one ridge waveguide junctions coupled to an output sub-wavelength grating coupler; and wherein the package shell has a void opening aligned with the output sub-wavelength grating coupler.

8. The packaged chip of claim 7, wherein the one or more resonance modes are unique along each of the one or more photonic crystal microcavity coupled waveguides.

9. The packaged chip of claim 7, wherein the substrate has a void opening aligned with the output sub-wavelength grating coupler or the cover polymer disposed on the slab has a void opening aligned with the output sub-wavelength grating coupler.

10. The packaged chip of claim 1, further comprising the input side of the one or more photonic crystal microcavity coupled waveguides coupled to one or more one-to-two ridge waveguide junctions; one of the one or more one-to-two ridge waveguide junctions coupled to an input sub-wavelength grating coupler; and wherein the package shell has a void opening aligned with the input sub-wavelength grating coupler.

11. The packaged chip of claim 1, further comprising a rigid dielectric cover disposed on the cover polymer between the cover polymer and the interior side of the top portion of the package shell.

12. The packaged chip of claim 1, wherein the substrate has a void opening aligned with the input sub-wavelength grating coupler or the cover polymer disposed on the slab has a void opening aligned with the input sub-wavelength grating coupler.

13. The packaged chip of claim 1, further comprising external optical fiber glued to the void openings with ultraviolet cured polymer.

14. The packaged chip of claim 13, wherein the facet of the external optical fiber is polished at an angle to enhance optical coupling efficiency.

15. The packaged chip of claim 14, wherein the facet of the external optical fiber is coated with a reflecting material.

16. The packaged chip of claim 15, wherein the reflecting material comprises gold.

17. The packaged chip of claim 1, wherein one or more analytes selectively bind to the one or more target binding molecules resulting in shifting the resonance frequencies of the one or more optical microcavities and hence the minima in the transmission spectrum of the one or more guided modes of the broadband source.

18. A packaged chip for the integration of arrays of photonic crystal slot waveguides with external optical sources and external optical detectors comprising:
  i) a package shell comprising a top portion, a bottom portion, and a side wall portion which together surround an interior volume;
  ii) a substrate disposed on the interior side of the bottom portion of the package shell and bounded by the interior side of the side wall portion of the package shell;
  iii) a bottom cladding disposed on the substrate and bounded by the interior side of the side wall portion of the package shell;
  iv) a slab disposed on the bottom cladding and bounded by the interior side of the side wall portion of the package shell, wherein the refractive index of the bottom cladding is lower than the refractive index of the slab;
  v) a cover polymer disposed on the slab, wherein the cover polymer is capped by the interior side of the top portion of the package shell and bounded by the interior side of the side wall portion of the package shell;
  vi) an input sub-wavelength grating coupler comprising a plurality of void columnar members with rectangular cross-section etched through the slab, wherein the plurality of void columnar members have a periodicity $\beta$ in one direction along of the slab and a periodicity $\gamma$ in the direction orthogonal to $\beta$ along the slab;
  vii) a first multimode interference power splitter comprising:
    a) a first input end;
    b) a first output end;
    c) a first rectangular mesa defined in the slab;
    d) wherein the first rectangular mesa is coupled by a first ridge waveguide to the input sub-wavelength grating coupler at the first input end of the first multimode interference power splitter; and
    e) wherein the first rectangular mesa is coupled to one or more ridge waveguides at the first output end of the first multimode interference power splitter;
  viii) a cascade of one or more multimode interference power splitters, wherein each of the one or more multimode interference power splitters comprises:
    a) an input end;
    b) an output end;
    c) a rectangular mesa defined in the slab;
    d) wherein the rectangular mesa at the input end of each of the one or more multimode interference power splitters is coupled to one of the one or more ridge waveguides at the first output end of the first multimode interference power splitter or to the output end of one or more multimode interference powers splitters; and
    e) wherein the rectangular mesa at the output end of each of the one or more multimode interference power splitters is coupled to one or more ridge waveguides;
  ix) one or more mode converters along the slab comprising a slotted ridge waveguide at the output of each mode converter and a ridge waveguide at the input of each mode converter, wherein the mode converter transforms the optical mode from the ridge waveguide mode to a slotted ridge waveguide mode;
  x) one or more photonic crystal slot waveguides comprising:
    a) an input side, wherein the input side is coupled to the output of one of the one or more mode converters;
    b) an output side;
    c) a plurality of void columnar members with circular cross-section etched through the slab;
    d) a core in the slab formed by a row of void columnar members, wherein the row of void columnar members is filled with the material of the slab and wherein the plurality of void columnar members surround the core in the slab and form a periodic triangular or square lattice comprising one or more lattice constants, $\alpha$s;
    e) one or more void slots within the core, extending the entire length of the core;
  xi) wherein the one or more photonic crystal slot waveguides support one or more guided modes of a broadband source and further comprises a region where the electric field intensity of the coupled electromagnetic radiation of the broadband source is enhanced and the group velocity of the coupled electromagnetic radiation of the broadband source is lowered;

xii) wherein an output transmission spectrum intensity of the coupled electromagnetic radiation of the broadband source varies as a function of the absorbance of an analyte within the one or more photonic crystal slot waveguides;

xiii) wherein, the cover polymer disposed on the slab has void openings above the area of the one or more photonic crystal slot waveguides; and xiv) wherein, the package shell has void openings aligned with the input sub-wavelength grating coupler.

19. The packaged chip of claim 18, further comprising:
i) an output mode converter along the slab comprising a slotted ridge waveguide at the input of the output mode converter and a ridge waveguide at the output of the output mode converter, wherein the output mode converter transforms the optical mode from the slotted ridge waveguide mode to a ridge waveguide mode;
ii) the output side of the one or more photonic crystal slot waveguides coupled to the slotted ridge waveguide at the input of the output mode converter; and
iii) the ridge waveguide at the output of the output mode converter coupled to an output sub-wavelength grating coupler and wherein the top of the package shell has a void opening aligned with the output sub-wavelength grating coupler.

20. The packaged chip of claim 19, wherein the substrate has a void opening aligned with the output sub-wavelength grating coupler or the cover polymer disposed on the slab has a void opening aligned with the output sub-wavelength grating coupler.

21. The packaged chip of claim 18, further comprising one or more multimode interference power combiners comprising:
i) an input end;
ii) an output end;
iii) a rectangular mesa defined in the slab;
iv) wherein the rectangular mesa at the input end of one of the one or more multimode interference power combiners is coupled by a ridge waveguide to the output side of the one or more photonic crystal slot waveguides or the output end of one of the one or more multimode interference power combiners;
v) wherein the rectangular mesa at the output end of the one or more multimode interference power combiners is coupled to one or more output sub-wavelength grating couplers; and
vi) wherein the top of the package shell has void openings aligned with the one or more output sub-wavelength grating couplers.

22. The packaged chip of claim 21, wherein the substrate has voided openings aligned with the one or more output sub-wavelength grating couplers or the cover polymer disposed on the slab has void openings aligned with the one or more output sub-wavelength grating couplers.

23. The packaged chip of claim 18, further comprising the slotted ridge waveguide at the output of each mode converter at the output side of the one or more photonic crystal slot waveguides coupled to one or more two-to-one ridge waveguide junctions; one of the one or more two-to-one ridge waveguide junctions coupled to an output sub-wavelength grating coupler; and wherein the top of the package shell has a void opening aligned with the output sub-wavelength grating coupler.

24. The packaged chip of claim 23, wherein the substrate has a void opening aligned with the output sub-wavelength grating coupler or the cover polymer disposed on the slab has a void opening aligned with the output sub-wavelength grating coupler.

25. The packaged chip of claim 18, further comprising the ridge waveguide at the input of each mode converter at the input side of the one or more photonic crystal slot waveguides coupled to one or more one-to-two ridge waveguide junctions; one of the one or more one-to-two ridge waveguide junctions coupled to an input sub-wavelength grating coupler; and wherein the top of the package shell has a void opening aligned with the input sub-wavelength grating coupler.

26. The packaged chip of claim 18, further comprising a rigid dielectric cover disposed between the cover polymer and the interior side of the top portion of the package shell.

27. The packaged chip of claim 18, further comprising external optical fiber glued to the void openings with ultraviolet cured polymer.

28. The packaged chip of claim 27, wherein the facet of the external optical fiber is polished at an angle to enhance optical coupling efficiency.

29. The packaged chip of claim 28, wherein the facet of the external optical fiber is coated with a reflecting material.

30. The packaged chip of claim 29, wherein the reflecting material comprises gold.

31. The packaged chip of claim 18, wherein the one or more photonic crystal slot waveguides are covered with hydrophobic polymer.

* * * * *